(12) United States Patent
Skog

(10) Patent No.: US 12,186,460 B2
(45) Date of Patent: Jan. 7, 2025

(54) AIR DECONTAMINATION APPARATUS FOR HVAC SYSTEMS

(71) Applicant: David Vernon Skog, Cornelius, NC (US)

(72) Inventor: David Vernon Skog, Cornelius, NC (US)

( * ) Notice: Subject to any disclaimer, the term of this patent is extended or adjusted under 35 U.S.C. 154(b) by 716 days.

(21) Appl. No.: 17/362,146

(22) Filed: Jun. 29, 2021

(65) Prior Publication Data

US 2021/0402038 A1 Dec. 30, 2021

Related U.S. Application Data

(60) Provisional application No. 63/045,300, filed on Jun. 29, 2020.

(51) Int. Cl.
*A61L 9/14* (2006.01)
*A61L 9/012* (2006.01)
*F24F 8/00* (2021.01)

(52) U.S. Cl.
CPC ............... *A61L 9/145* (2013.01); *A61L 9/012* (2013.01); *F24F 8/00* (2021.01); *A61L 2209/111* (2013.01); *A61L 2209/134* (2013.01); *A61L 2209/14* (2013.01); *A61L 2209/15* (2013.01); *A61L 2209/16* (2013.01)

(58) Field of Classification Search
CPC ... A61L 9/00; A61L 9/01; A61L 9/012; A61L 9/145; A61L 2209/00; A61L 2209/10; A61L 2209/11; A61L 2209/111; A61L 2209/13; A61L 2209/134; A61L 2209/14; A61L 2209/15; A61L 2209/16; F24F 7/00; F24F 7/003; F24F 8/00; F24F 8/10; F24F 8/117; F24F 8/133; F24F 8/20; F24F 13/00; F24F 13/28
See application file for complete search history.

(56) References Cited

U.S. PATENT DOCUMENTS

| | | | | |
|---|---|---|---|---|
| 5,066,328 | A | * 11/1991 | Zlotnik | ................... A01N 25/24 106/18.32 |
| 5,314,719 | A | 5/1994 | Batdorf et al. | |
| 5,918,637 | A | * 7/1999 | Fleischman | ............ B01D 3/008 138/40 |
| 7,824,626 | B2 | 11/2010 | Kwiatkowski | |
| 8,016,651 | B2 * | 9/2011 | Mangiapane | ...... B60H 1/00792 454/139 |
| 8,696,803 | B1 | 4/2014 | Knapp, III et al. | |
| 9,689,580 | B2 | 6/2017 | Burke et al. | |
| 10,251,969 | B2 | 4/2019 | Prax | |

(Continued)

FOREIGN PATENT DOCUMENTS

CN 208967778 U * 6/2019

*Primary Examiner* — Natasha E Young
(74) *Attorney, Agent, or Firm* — Jeffrey C. Watson, Esq.; Grell & Watson Patent Attorneys LLC

(57) ABSTRACT

An air decontamination apparatus for a common HVAC system includes a plurality of venturi holes. The plurality of venturi holes are configured to be positioned in the common HVAC system for forcing airflow in the common HVAC system through the plurality of venturi holes. Each of the plurality of venturi holes including an antimicrobial coating. Wherein, the air decontamination apparatus is configured to kill bacteria and viruses in the airflow in the common HVAC system via the antimicrobial coating on each of the plurality of venturi holes.

18 Claims, 22 Drawing Sheets

(56) References Cited

U.S. PATENT DOCUMENTS

| | | |
|---|---|---|
| 10,343,496 B2 | 7/2019 | Chapaton et al. |
| 10,512,872 B2 | 12/2019 | Williams et al. |
| 10,584,885 B2 | 3/2020 | Burke et al. |
| 10,632,411 B2 | 4/2020 | Williams et al. |

* cited by examiner

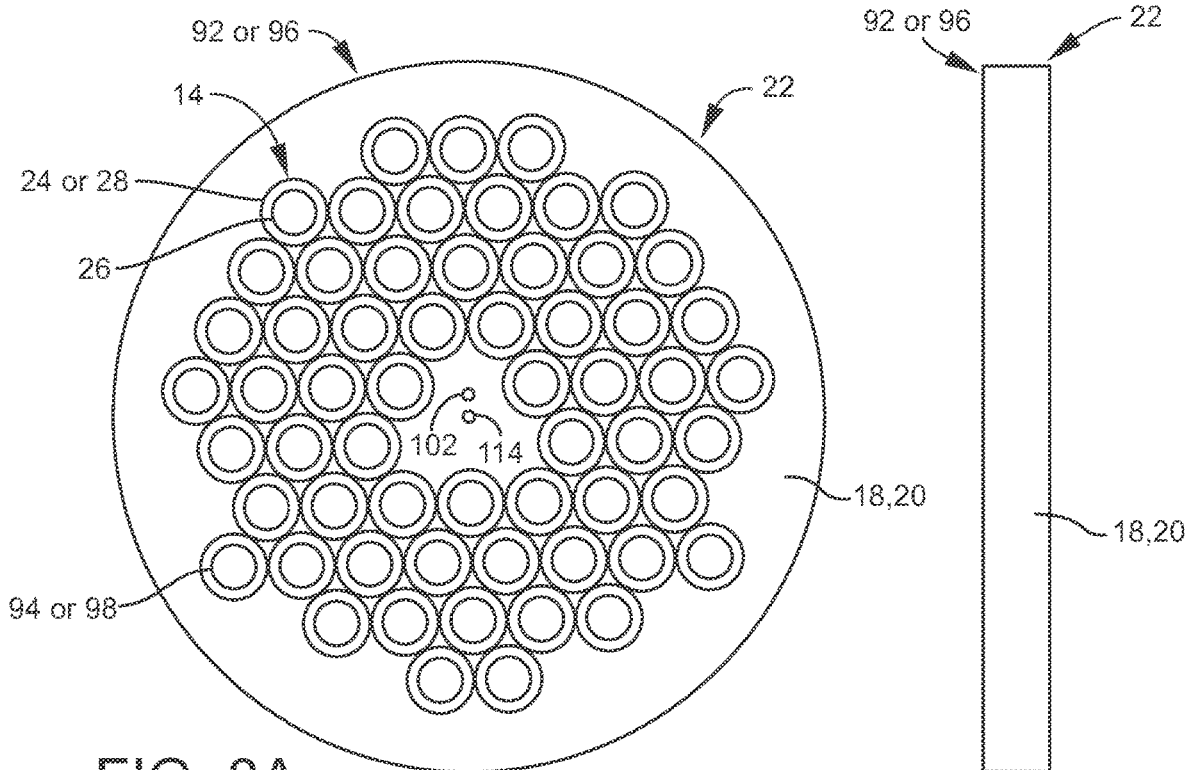
FIG. 8A
FIG. 8C
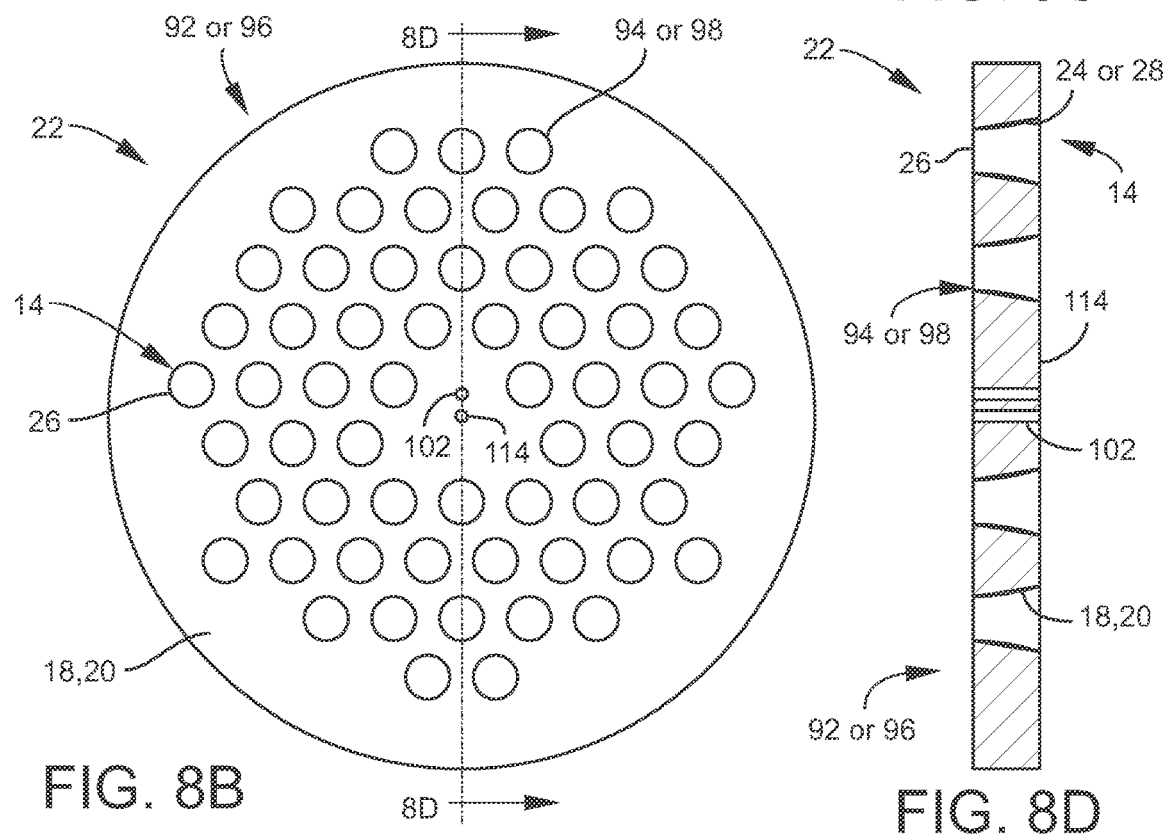
FIG. 8B
FIG. 8D

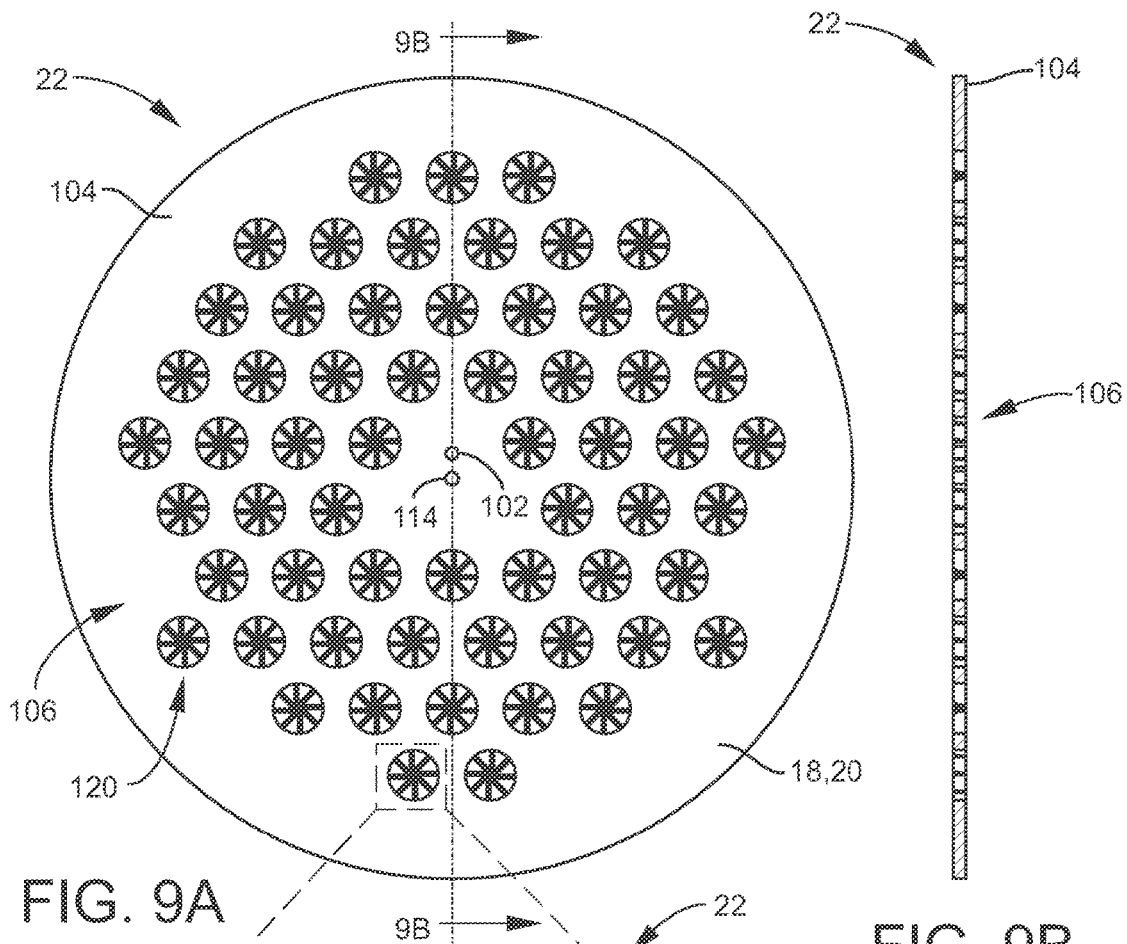
FIG. 9A
FIG. 9B
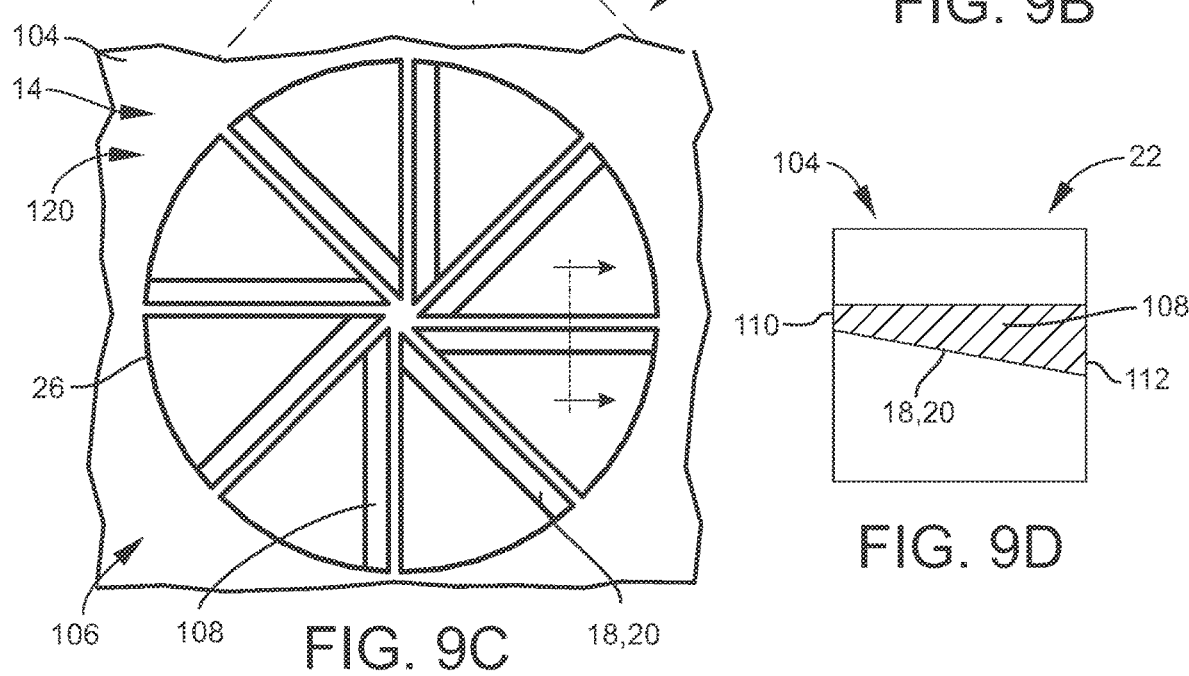
FIG. 9C
FIG. 9D

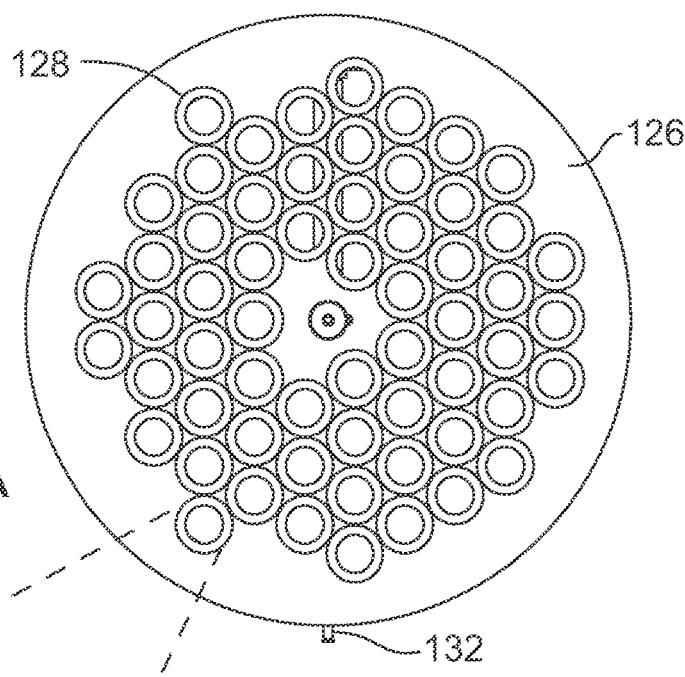
FIG. 20A
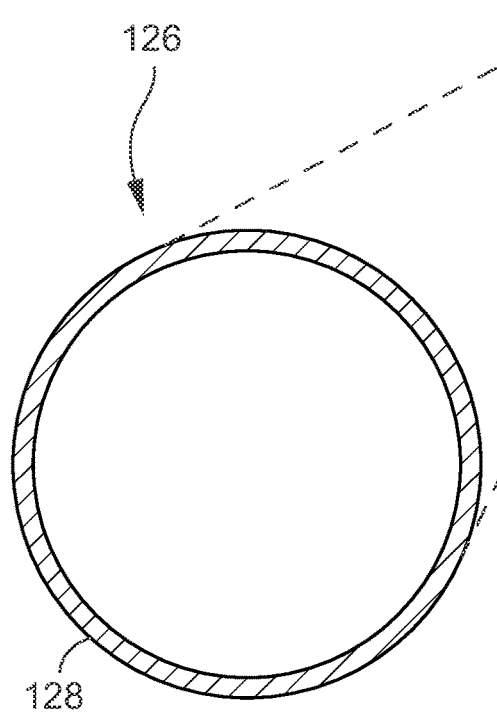
FIG. 20B
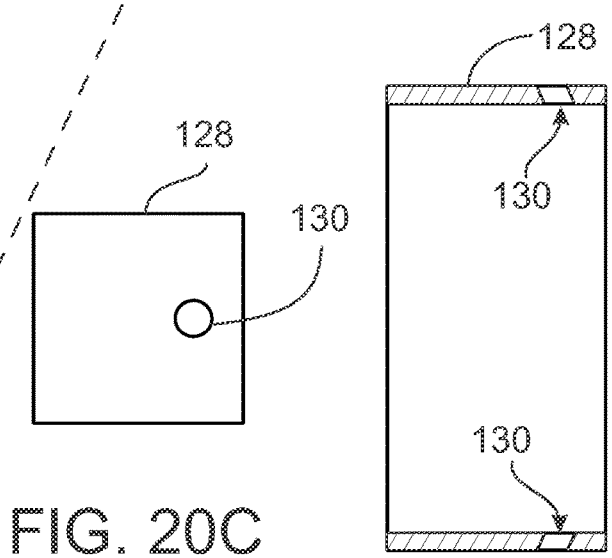
FIG. 20C
FIG. 20D
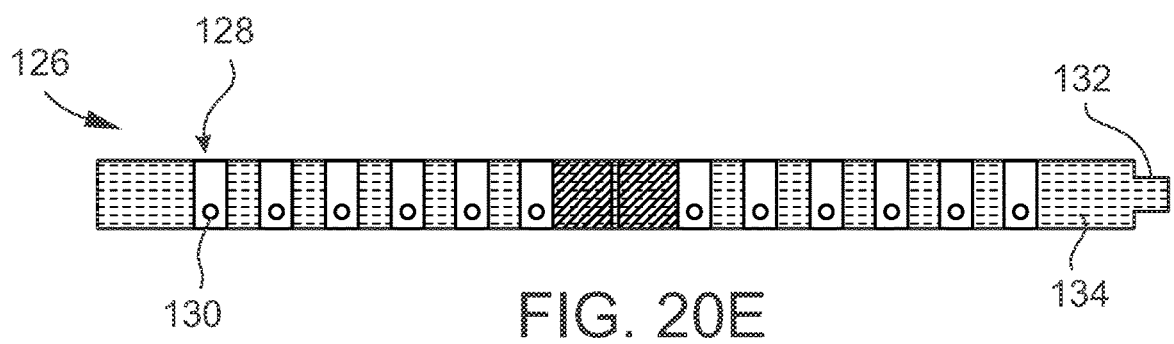
FIG. 20E

AIR DECONTAMINATION APPARATUS FOR HVAC SYSTEMS

CROSS-REFERENCE TO RELATED APPLICATIONS

This application claims benefit to U.S. Provisional Patent Application No. 63/045,300, filed on Jun. 29, 2020, which is incorporated by reference in its entirety.

FIELD OF THE DISCLOSURE

The present disclosure is related to heating, ventilation and air conditioning systems, also called HVAC systems. More specifically, the present disclosure is directed toward an air decontamination apparatus for HVAC systems.

BACKGROUND

Generally speaking, heating, ventilation, and air conditioning systems, or HVAC systems, is the technology of indoor and vehicular environmental comfort. Its goal is to provide thermal comfort and acceptable indoor air quality. HVAC system design is a subdiscipline of mechanical engineering, based on the principles of thermodynamics, fluid mechanics and heat transfer. HVAC is an important part of residential structures such as single-family homes, apartment buildings, hotels and senior living facilities, medium to large industrial and office buildings such as skyscrapers and hospitals, vehicles such as cars, trains, airplanes, ships and submarines, and in marine environments, where safe and healthy building conditions are regulated with respect to temperature and humidity, using fresh air from outdoors.

Ventilating or ventilation (the "V" in HVAC) is the process of exchanging or replacing air in any space to provide high indoor air quality which involves temperature control, oxygen replenishment, and removal of moisture, odors, smoke, heat, dust, airborne bacteria, carbon dioxide, and other gases. Ventilation removes unpleasant smells and excessive moisture, introduces outside air, keeps interior building air circulating, and prevents stagnation of the interior air.

In recent times with the COVID-19 pandemic affecting the world, the need to control or decontaminate bacterial micro-organisms and viruses are of utmost importance, especially airborne bacterial micro-organisms and viruses. Although most HVAC systems include some form of filtration, most air borne bacterial micro-organisms and viruses are not affected or filtered with most common HVAC filtration systems. Therefore, a need clearly exists for a device, means and/or apparatus configured to aid in filtering or decontaminating the air or environment of a common HVAC system to help or aid in filtering, removing, killing, decontaminating, the like, etc. any airborne bacterial micro-organisms and viruses running through such HVAC system.

The instant disclosure may be designed to address at least certain aspects of the problems or needs discussed above by providing an air decontamination apparatus for HVAC systems.

SUMMARY

The present disclosure may solve the aforementioned limitations of the currently available filtering or decontamination devices, apparatus, means and/or methods for filtering, removing, killing, decontaminating, the like, etc. any airborne bacterial micro-organisms and/or viruses in the air or environment of a common HVAC system, by providing an air decontamination apparatus. The air decontamination apparatus may be designed and/or configured for a common HVAC system. The air decontamination apparatus may generally include a plurality of venturi holes. The plurality of venturi holes may be configured to be positioned in the common HVAC system for forcing airflow in the common HVAC system through the plurality of venturi holes. Each of the plurality of venturi holes may include an antimicrobial coating. Wherein, the air decontamination apparatus is configured to remove, kill, filter, decontaminate, the like, etc. any bacteria and viruses in the airflow in the common HVAC system via the antimicrobial coating on each of the plurality of venturi holes.

One feature of the disclosed air decontamination apparatus for HVAC systems may be that the antimicrobial coating can be an electrostatic antimicrobial. The electrostatic antimicrobial coating may be applied to all surfaces of the air decontamination apparatus, including, but not limited to, all portions of each of the plurality of venturi holes.

In select embodiments of the disclosed air decontamination apparatus for HVAC systems, a venturi plate device may be included. The venturi plate device may include the plurality of venturi holes. Each of the plurality of venturi holes in the venturi plate device may include a wide inlet portion, a narrow middle portion, and a wide exhaust portion. Where, the wide inlet portion tapers into the narrow middle portion and the narrow middle portion tapers out to the wide exhaust portion. Wherein, the venturi plate device may be configured to be sealed between an inlet of the common HVAC system or an outlet of the common HVAC system for forcing the airflow of the common HVAC system through each of the plurality of venturi holes in the venturi plate device. As such, the venturi plate device may be sized and configured to be sealed to a duct of the common HVAC system in the inlet or the outlet of the common HVAC system. In select embodiments, the venturi plate device may be sealed to the duct of the common HVAC system in the inlet or the outlet of the common HVAC system via a foam seal around the venturi plate device.

Another feature of the disclosed air decontamination apparatus for HVAC systems may be the inclusion of a mounting bracket. The mounting bracket may be designed and/or configured to secure the venturi plate device to be sealed between the inlet of the common HVAC system or the outlet of the common HVAC system. In select embodiments, the mounting bracket may be configured to be mounted inside a duct of the common HVAC system for sealing the venturi plate device to the duct. In such select embodiments, the mounting bracket may include an upper mount, a lower mount, an adjustable rod bracket, and a mounting plate. The upper mount may have an upper foam pad. The upper foam pad can include an adhesive configured to secure the upper mount to a first portion of an inside of the duct. Likewise, the lower mount may have a lower foam pad. The lower foam pad can include the adhesive configured to secure the lower mount to a second portion of the inside of the duct. The second portion may be on an opposite side of the duct from the first portion. The adjustable rod bracket may be connected between the upper mount and the lower mount. The mounting plate may be connected to the adjustable rod bracket. The mounting plate may be configured to secure the venturi plate device to the adjustable rod bracket connected between the upper mount and the lower mount.

In select embodiments, the adjustable rod bracket can include a pair of inner rods and a pair of outer rods. The pair of inner rods may be connected to the upper mount, and the pair of outer rods may be connected to the lower mount (or vice versa). In this embodiment, the mounting plate may include an upper clamp plate and a lower clamp plate. The upper clamp plate can include four upper half-round cuts and a plurality of threaded holes (i.e., 4 threaded holes). The lower clamp plate can include four lower half-round cuts configured to mirror the four upper half-round cuts, and a plurality of counterbore holes (i.e., 4 counterbore holes) configured to align with the plurality of threaded holes in the upper clamp plate. A mounting alignment dowel may protrude from the lower clamp plate. A mounting stud may be secured to the lower clamp plate through a center hole in the lower clamp plate. Wherein, the mounting plate may be configured to be adjustably secured to the pair of inner rods and the pair of outer rods via the lower clamp plate being secured to the upper clamp plate and squeezed around the pair of inner rods and the pair of outer rods in between the four upper half-round cuts and the four lower half-round cuts via a plurality of screws connected between the plurality of threaded holes in the upper clamp plate and the plurality of counterbore holes in the lower clamp plate. In select embodiments, the mounting stud may be configured to connect the venturi plate device to the mounting plate via a threaded connection to a knob with a knurled outer diameter. In other select embodiments, the mounting alignment dowel may be configured to align the venturi plate device about the mounting plate via an alignment hole in the venturi plate device.

In select embodiments of the disclosed air decontamination apparatus for HVAC systems, the venturi plate device may include an inlet venturi plate and an exhaust venturi plate. The inlet venturi plate may include the wide inlet portion of each of the plurality of venturi holes and a narrow inlet portion of the narrow middle portion of each of the plurality of venturi holes. The exhaust venturi plate may have the wide exhaust portion of each of the plurality of venturi holes and a narrow exhaust portion of the narrow middle portion of each of the plurality of venturi holes. The narrow inlet portions of each of the narrow middle portions in the inlet venturi plate may be aligned and fluidly connected to the narrow exhaust portions of each of the narrow middle portions of the exhaust venturi plate. In select embodiments, a plate alignment dowel may be included. The plate alignment dowel may protrude from the inlet venturi plate and into an alignment hole of the exhaust venturi plate, or vice versa. The plate alignment dowel may be configured to align each of the plurality of narrow inlet portions in the inlet venturi plate with each of the narrow exhaust portions in the exhaust venturi plate for creating the plurality of venturi holes therebetween. In select embodiments, the inlet venturi plate and the exhaust venturi plate may be completely coated with the antimicrobial coating.

One feature of the disclosed air decontamination apparatus for HVAC systems may be the inclusion of an intermediate antimicrobial plate. The intermediate antimicrobial plate may be positioned between the inlet venturi plate and the exhaust venturi plate. The intermediate antimicrobial plate may include a plurality of bladed holes. The plurality of bladed holes may be configured to be positioned between the narrow inlet portions in the inlet venturi plate and the narrow exhaust portions in the exhaust venturi plate. In select embodiments, each of the plurality of bladed holes may include a plurality of turbulence blades. Each turbulence blade may include a sharp inlet edge angled toward a wider exit edge. Each turbulence blade of each of the plurality of bladed holes may include the antimicrobial coating. Wherein, the intermediate antimicrobial plate may be configured to swirl the airflow through the plurality of venturi holes. In select embodiments, the intermediate antimicrobial plate may further include a center through hole configured to receive a mounting stud. An intermediate alignment hole may also be included that is configured to receive the plate alignment dowel therethrough, thereby aligning the plurality of bladed holes between the narrow inlet portions in the inlet venturi plate and the narrow exhaust portions in the exhaust venturi plate. The entire intermediate antimicrobial plate may include the antimicrobial coating. In select embodiments, each of the plurality of bladed holes may include eight turbulence blades equally spaced for creating a fan design.

Another feature of the disclosed air decontamination apparatus for HVAC systems may be the inclusion of an antimicrobial liquid injection system. The antimicrobial liquid injection system may be configured to insert an antimicrobial liquid into the airflow moving through each of the venturi holes of the venturi plate device. In select embodiments, the antimicrobial liquid injection system may include a liquid intermediate plate. The liquid intermediate plate may be positioned between the inlet venturi plate and the exhaust venturi plate. In select embodiments, the intermediate antimicrobial plate may include a plurality of injection holes configured to be positioned between the narrow inlet portions in the inlet venturi plate and the narrow exhaust portions in the exhaust venturi plate. Each of the plurality of injection holes may include at least one fluid port. Wherein, the liquid intermediate plate may be configured to insert the antimicrobial liquid into the airflow through the plurality of venturi holes via the at least one fluid port in each of the plurality of injection holes. In select embodiments, the liquid intermediate plate may further include at least one hose port configured to communicate with a hollow interior of the liquid intermediate plate. The hollow interior of the liquid intermediate plate may fluidly connect each of the at least one hose ports with each of the fluid ports in each of the plurality of injection holes. In other select embodiments of the liquid intermediate plate, a center through hole may be included that may be configured to receive the mounting stud. In other select embodiments of the liquid intermediate plate, an intermediate alignment hole may be included that can be configured to receive the plate alignment dowel therethrough, thereby aligning the plurality of injection holes between the narrow inlet portions in the inlet venturi plate and the narrow exhaust portions in the exhaust venturi plate. In select embodiments, the entire liquid intermediate plate may include the antimicrobial coating. In select embodiments, each of the plurality of injection holes may include four fluid ports equally spaced around the injection hole, and each of the plurality of injection holes may be angled from the wide inlet portions toward the wide exhaust portions of the venturi holes.

In select embodiments of the disclosed air decontamination apparatus, the antimicrobial liquid injection system may further include a reservoir, a hose, and a reservoir mounting bracket. The reservoir may be configured to hold the antimicrobial liquid. The hose may be connected between the reservoir and the at least one hose port of the liquid intermediate plate. The reservoir mounting bracket may be configured to hold the reservoir and be mounted to the inside of a filter housing of the common HVAC system via adhesive strips. In select embodiments, the antimicrobial liquid injection system may further include a fluid level sensor in the reservoir. The fluid level sensor may be configured to sense the amount of the antimicrobial liquid inside of the reservoir. In select embodiments, a buzzer may also be included. The buzzer may be in communication with the fluid level sensor. The buzzer may be configured to emit an alarm sound when the fluid level sensor senses the amount of the antimicrobial liquid inside of the reservoir is below a set refill amount. In select embodiments of the antimicrobial liquid injection system, a battery may be included that can be configured to power the buzzer. The battery may be mounted on the reservoir via a battery holder. A positive connector wire may be connected between a positive side of the battery and the buzzer. A first negative connector wire may be connected between a negative side of the battery and the fluid level sensor. A second negative connector wire may be connected between the fluid level sensor and the buzzer. With this configuration, the fluid level sensor may be a normally closed fluid activated sensor configured to close when dry and open when wet. A low fluid level warning kit cover may be attached to a bottom of the reservoir configured to house and seal the battery, buzzer, and fluid level sensor.

One feature of the disclosed air decontamination apparatus for HVAC systems with the antimicrobial liquid injection system, may be that the antimicrobial liquid injection system may be configured to allow the antimicrobial liquid to be drawn out of each of the fluid ports in each of the injection holes via low pressure created by the airflow of the common HVAC system.

In another aspect, the instant disclosure embraces the disclosed air decontamination apparatus for HVAC system in any of the embodiments and/or combination of embodiments shown and/or described herein.

In another aspect, the instant disclosure embraces the disclosed air decontamination apparatus for HVAC system with the intermediate antimicrobial plate in any of the embodiments and/or combination of embodiments shown and/or described herein.

In another aspect, the instant disclosure embraces the disclosed air decontamination apparatus for HVAC system with the antimicrobial liquid injection system in any of the embodiments and/or combination of embodiments shown and/or described herein.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

The present disclosure will be better understood by reading the Detailed Description with reference to the accompanying drawings, which are not necessarily drawn to scale, and in which like reference numerals denote similar structure and refer to like elements throughout, and in which:

FIG. 8A shows a front view of an inlet venturi plate or a rear view of an exhaust venturi plate for the air decontamination apparatus for HVAC systems according to select embodiments of the instant disclosure;

FIG. 8B shows a rear view of the inlet venturi plate of FIG. 8A or a font view of the exhaust venturi plate of FIG. 8A;

FIG. 8C shows a side view of the inlet venturi plate of FIG. 8A or the exhaust venturi plate of FIG. 8A;

FIG. 8D shows a cross-sectional view of the inlet venturi plate of FIG. 8B or the exhaust venturi plate of FIG. 8B;

FIG. 9A shows a front view of an intermediate antimicrobial plate for the air decontamination apparatus for HVAC systems according to select embodiments of the instant disclosure;

FIG. 9B shows a cross-sectional view of the intermediate antimicrobial plate of FIG. 9A;

FIG. 9C shows a zoomed in view of the bladed holes of the intermediate antimicrobial plate of FIG. 9A;

FIG. 9D shows a cross-sectional view of the turbulence blades from the bladed holes of FIG. 9C;

FIG. 20A shows a front view of the liquid intermediate plate according to select embodiments of the instant disclosure for the air decontamination apparatus for HVAC systems;

FIG. 20B shows a zoomed in view of one of the fluid ports from the liquid intermediate plate from FIG. 20A;

FIG. 20C shows a top cross-sectional view of one of the liquid ports from the liquid intermediate plate from FIG. 20A;

FIG. 20D shows a side cross-sectional view of one of the liquid ports from the liquid intermediate plate from FIG. 20A;

FIG. 20E shows a cross-sectional view of the liquid intermediate plate from FIG. 20A;

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

Referring now to FIGS. 1-24, in describing the exemplary embodiments of the present disclosure, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples and are merely examples among other possible examples.

Figure 1:
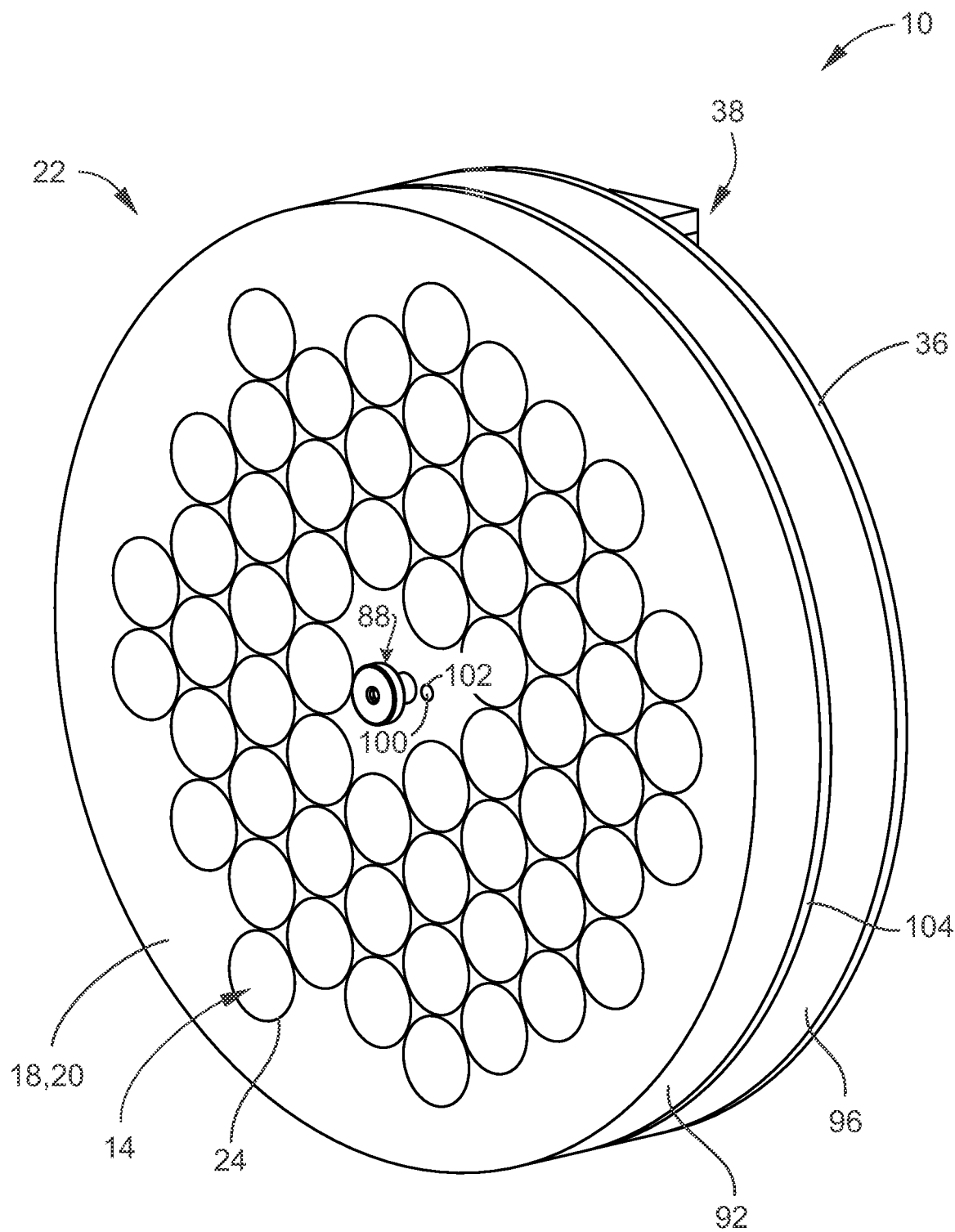
FIG. 1 shows a front perspective view of an air decontamination apparatus for HVAC systems according to select embodiments of the instant disclosure.
Figure 2:
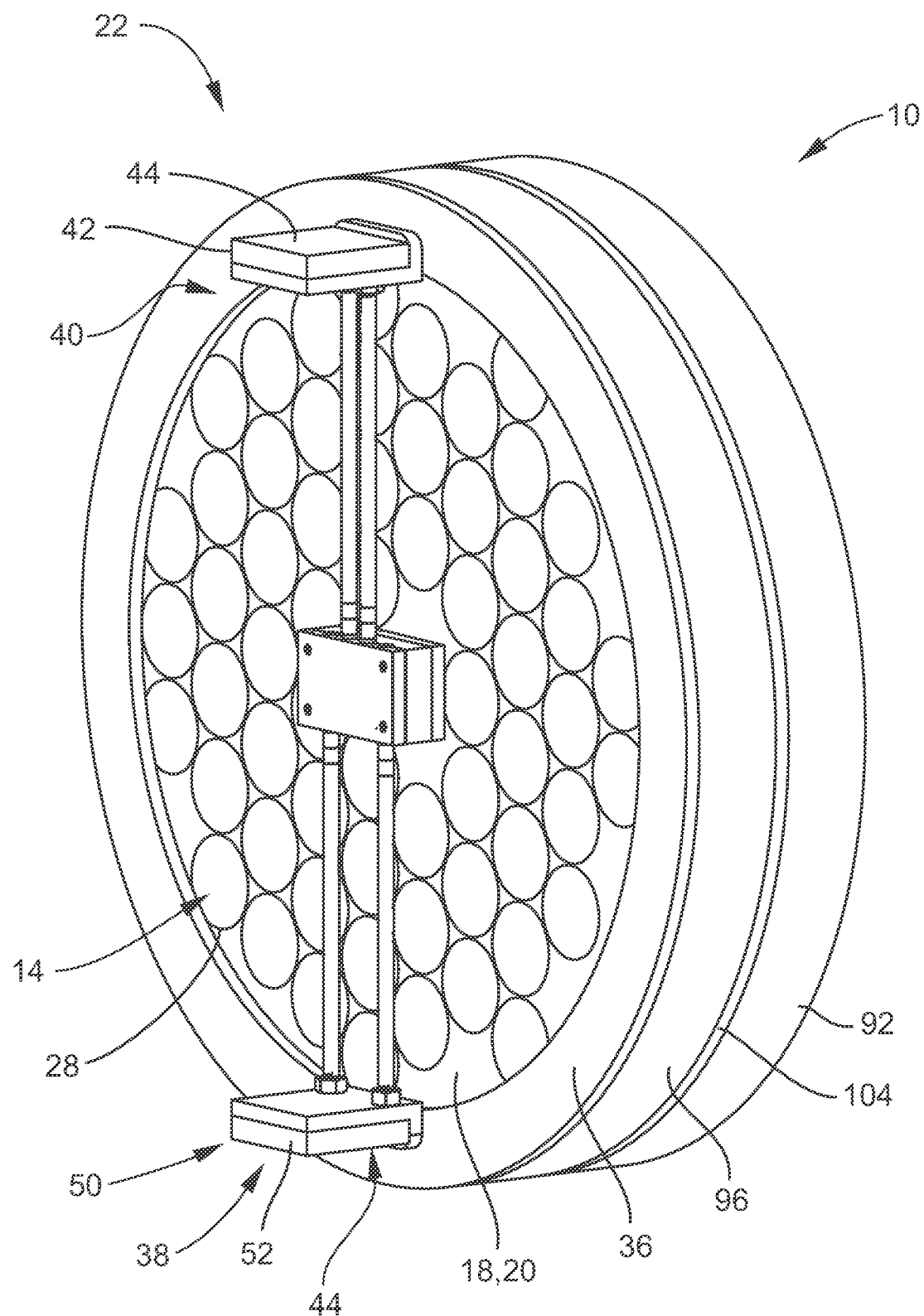
FIG. 2 shows a rear perspective view of the air decontamination apparatus for HVAC systems of FIG. 1.
Figure 3:
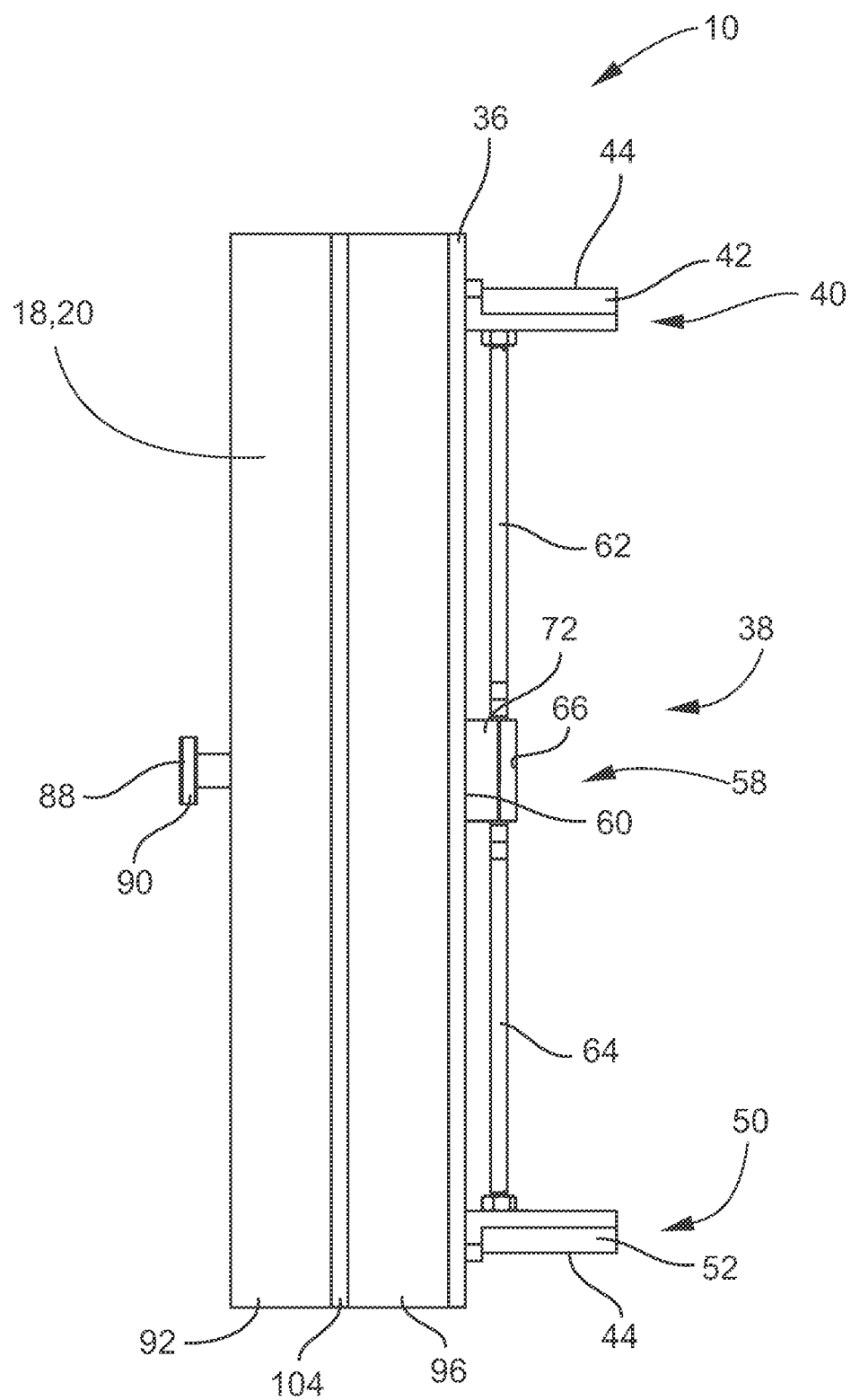
FIG. 3 shows a side view of the air decontamination apparatus for HVAC systems of FIG. 1.
Figure 4:
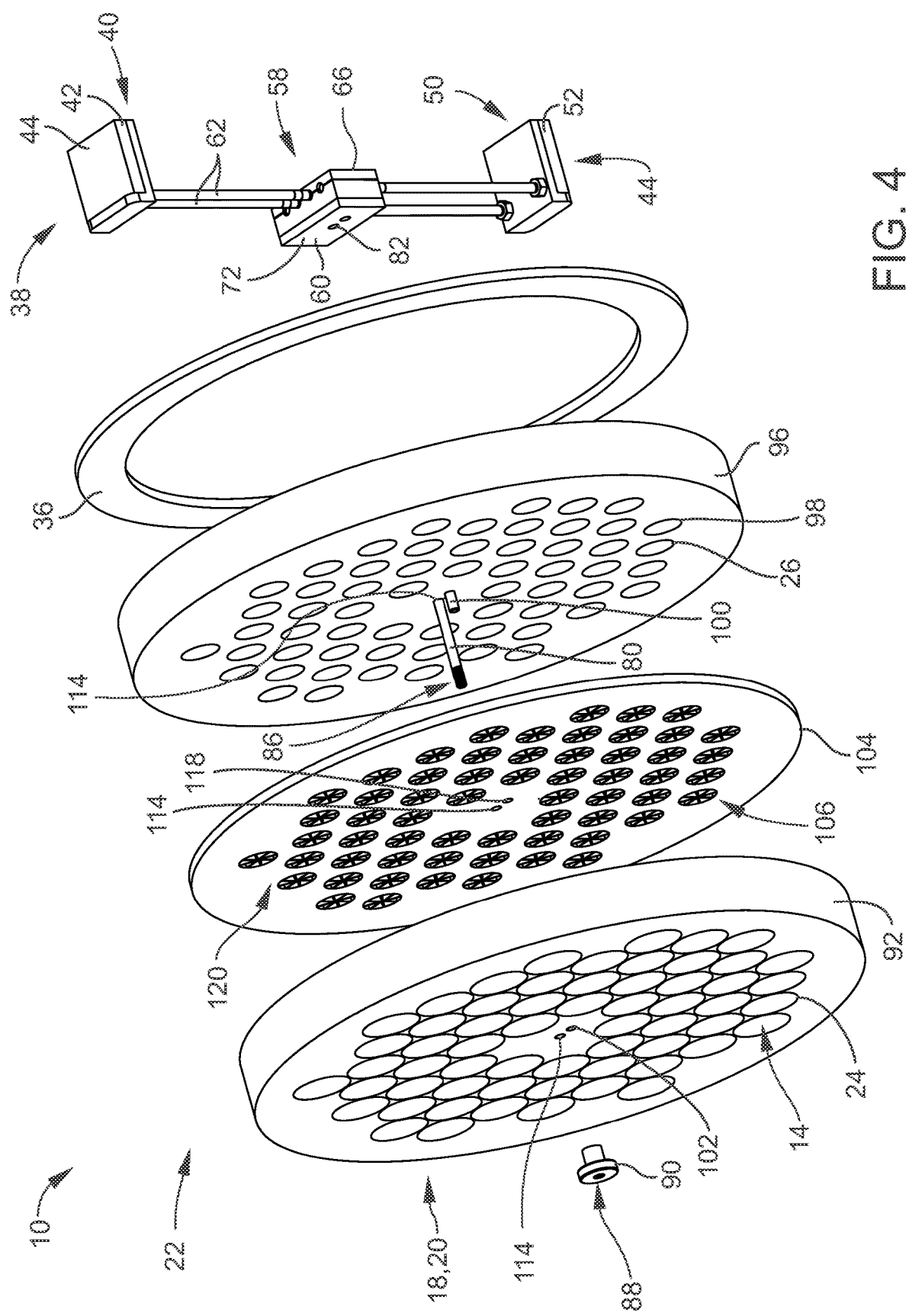
FIG. 4 shows a front perspective partially disassembled view of the air decontamination apparatus for HVAC systems of FIG. 1.
Figure 5:
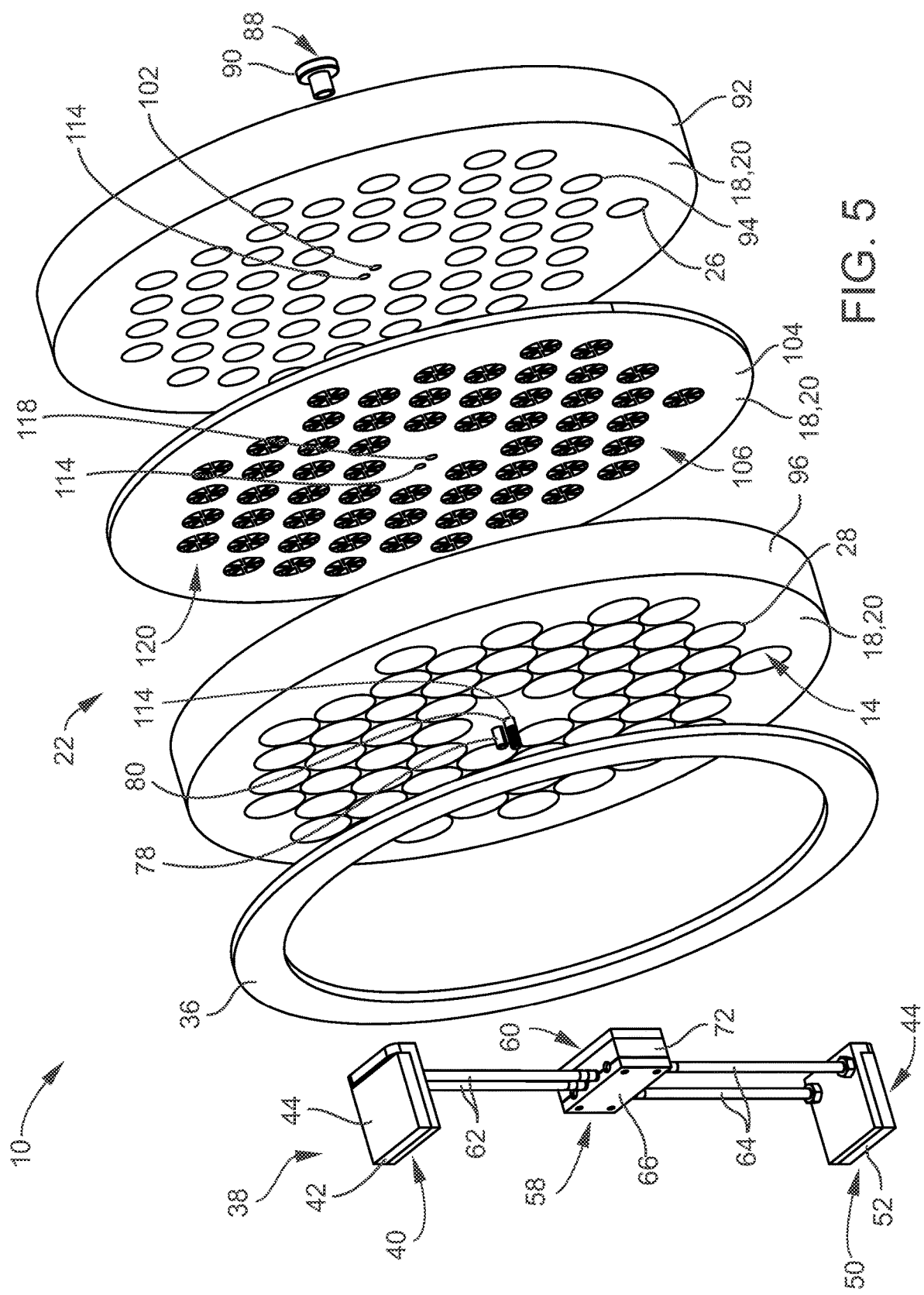
FIG. 5 shows a rear perspective partially disassembled view of the air decontamination apparatus for HVAC systems of FIG. 1.
Figure 6:
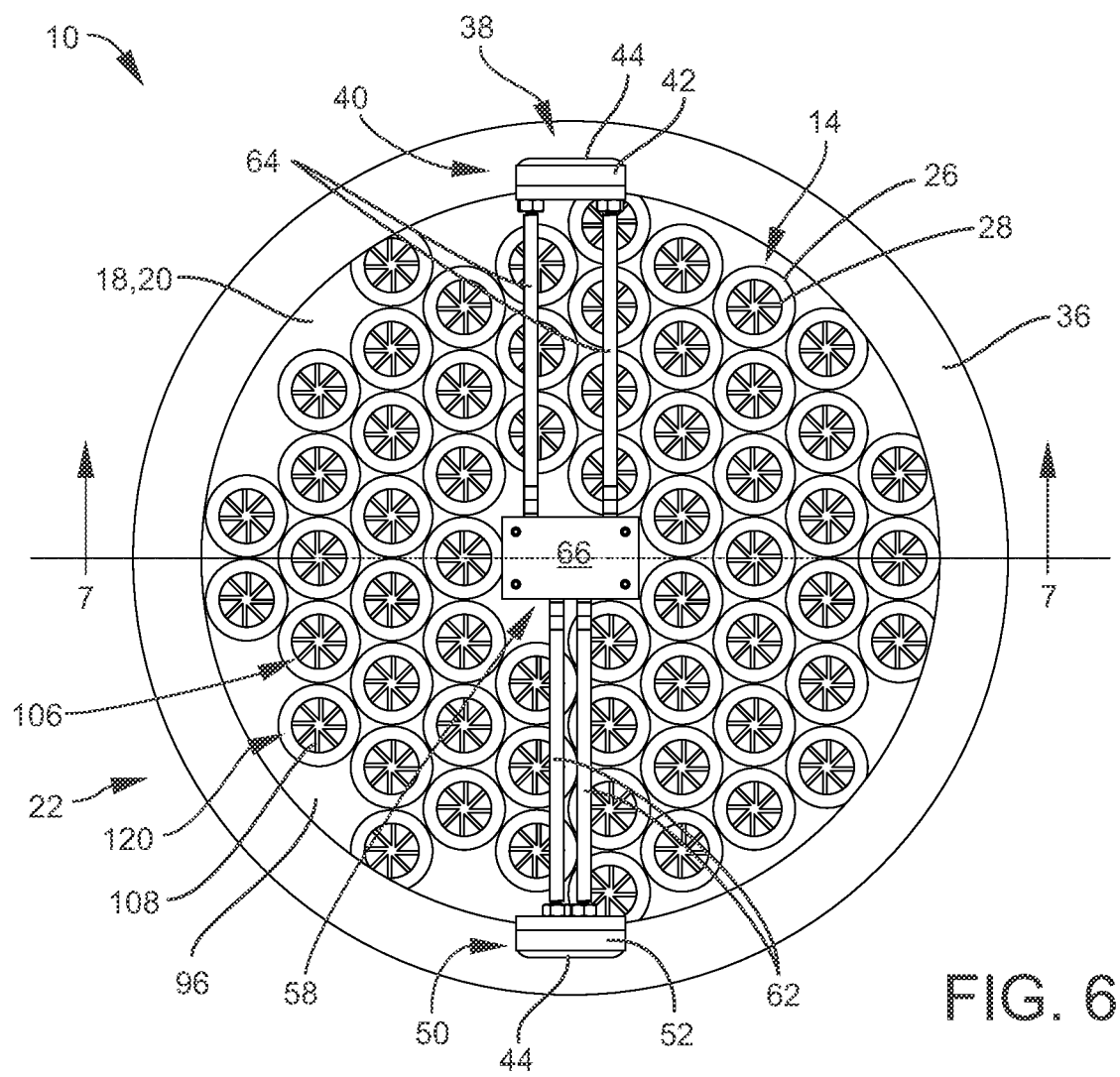
FIG. 6 shows a rear view of the air decontamination apparatus for HVAC systems of FIG. 1.
Figure 7:
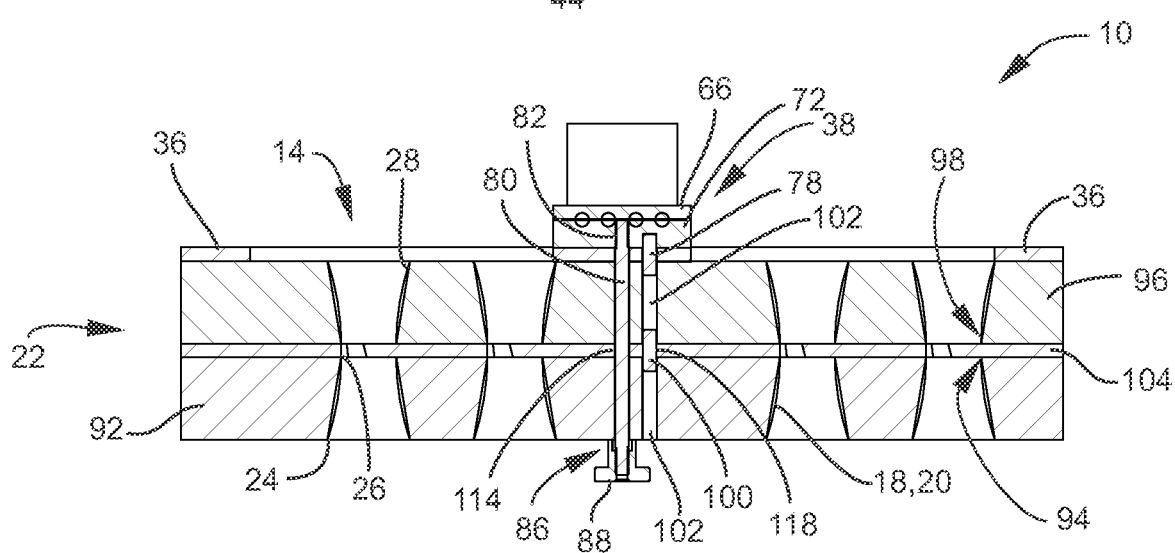
FIG. 7 shows a top cross-sectional view of the air decontamination apparatus for HVAC systems of FIG. 1.
Figure 10:
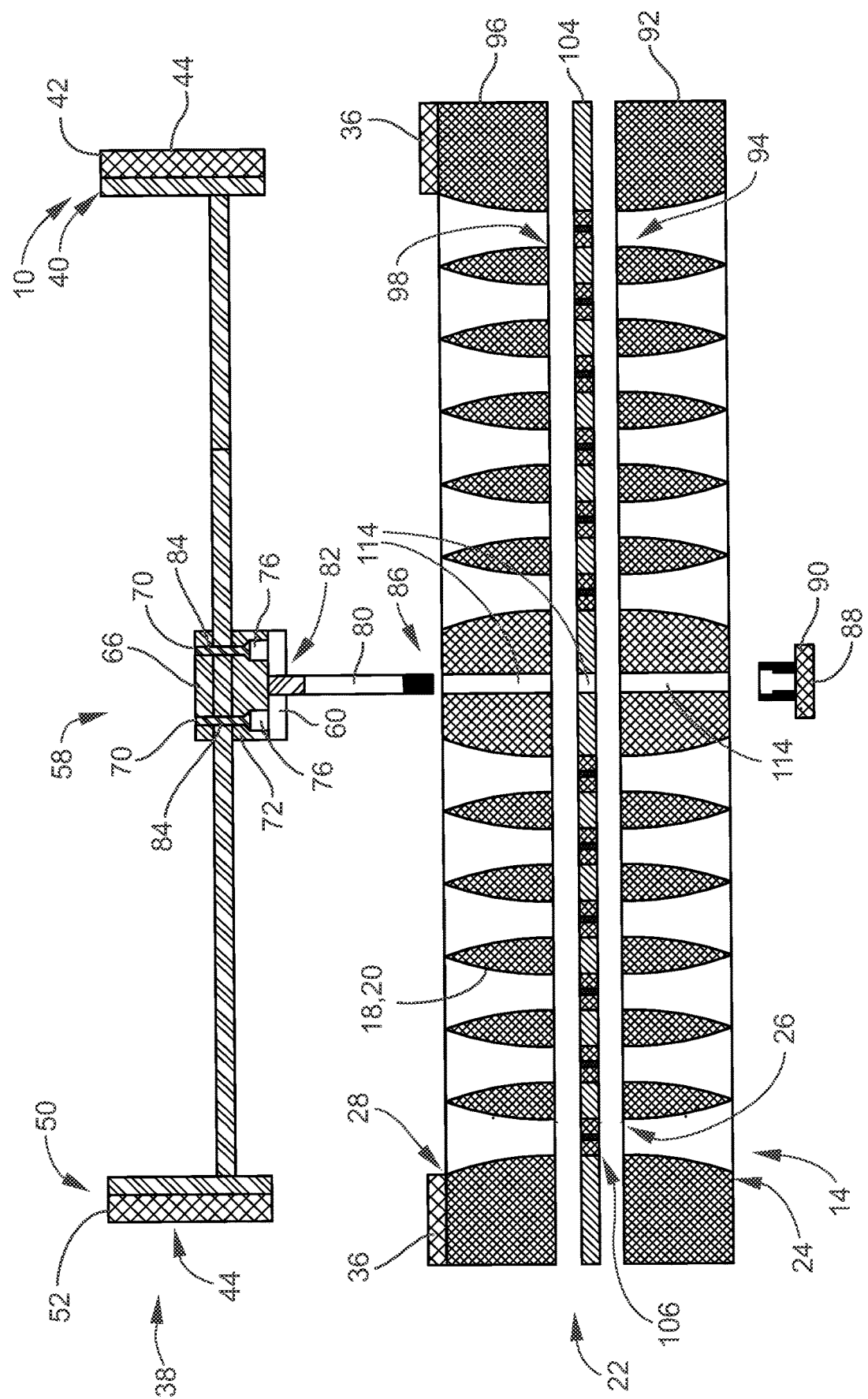
FIG. 10 shows a partially disassembled cross-sectional side view of the air decontamination apparatus for HVAC systems of FIG. 1.
Figure 11:
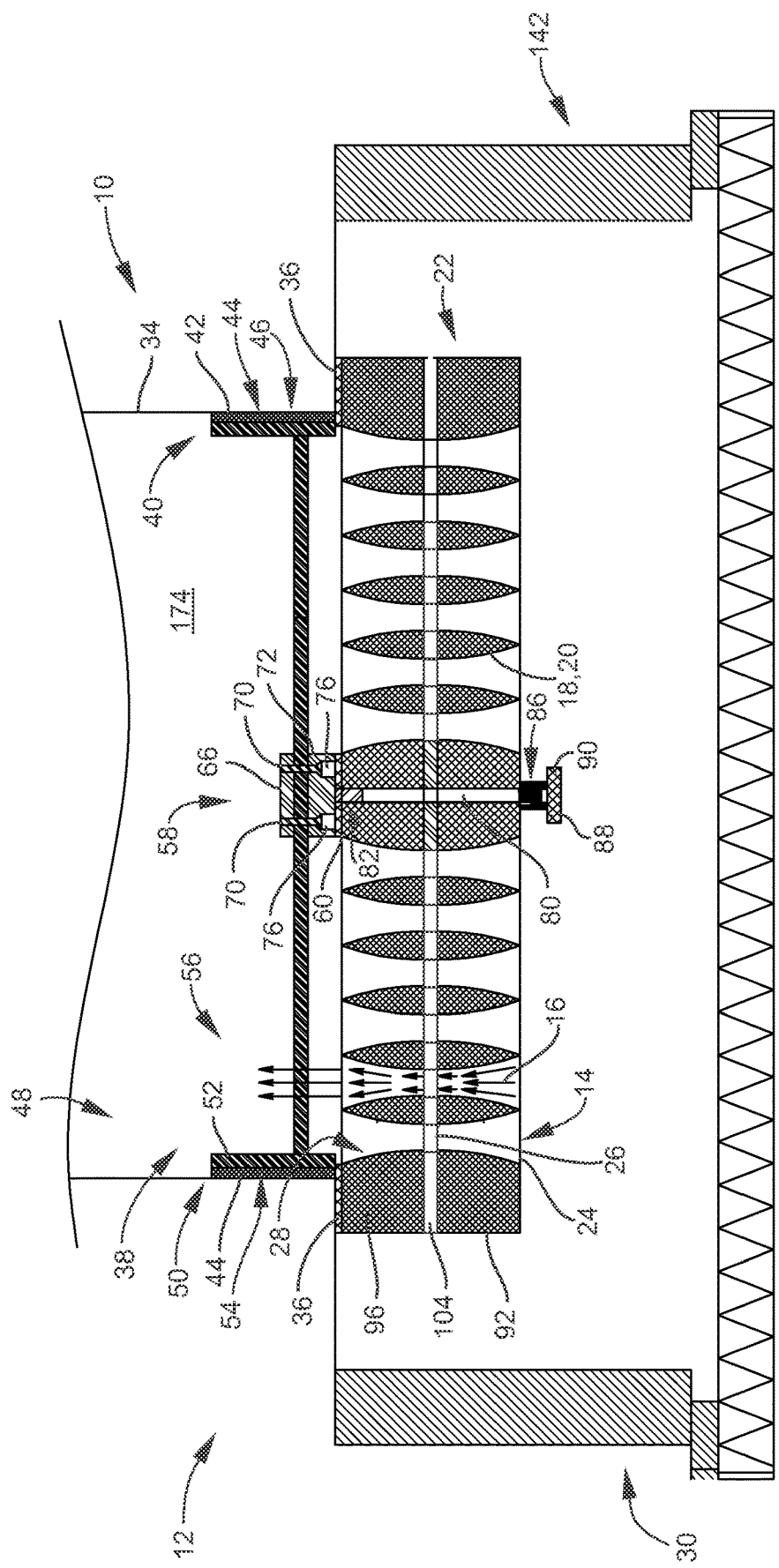
FIG. 11 shows a cross-sectional side view of the air decontamination apparatus for HVAC systems according to select embodiments of the instant disclosure installed into a common HVAC system.
Figure 22:
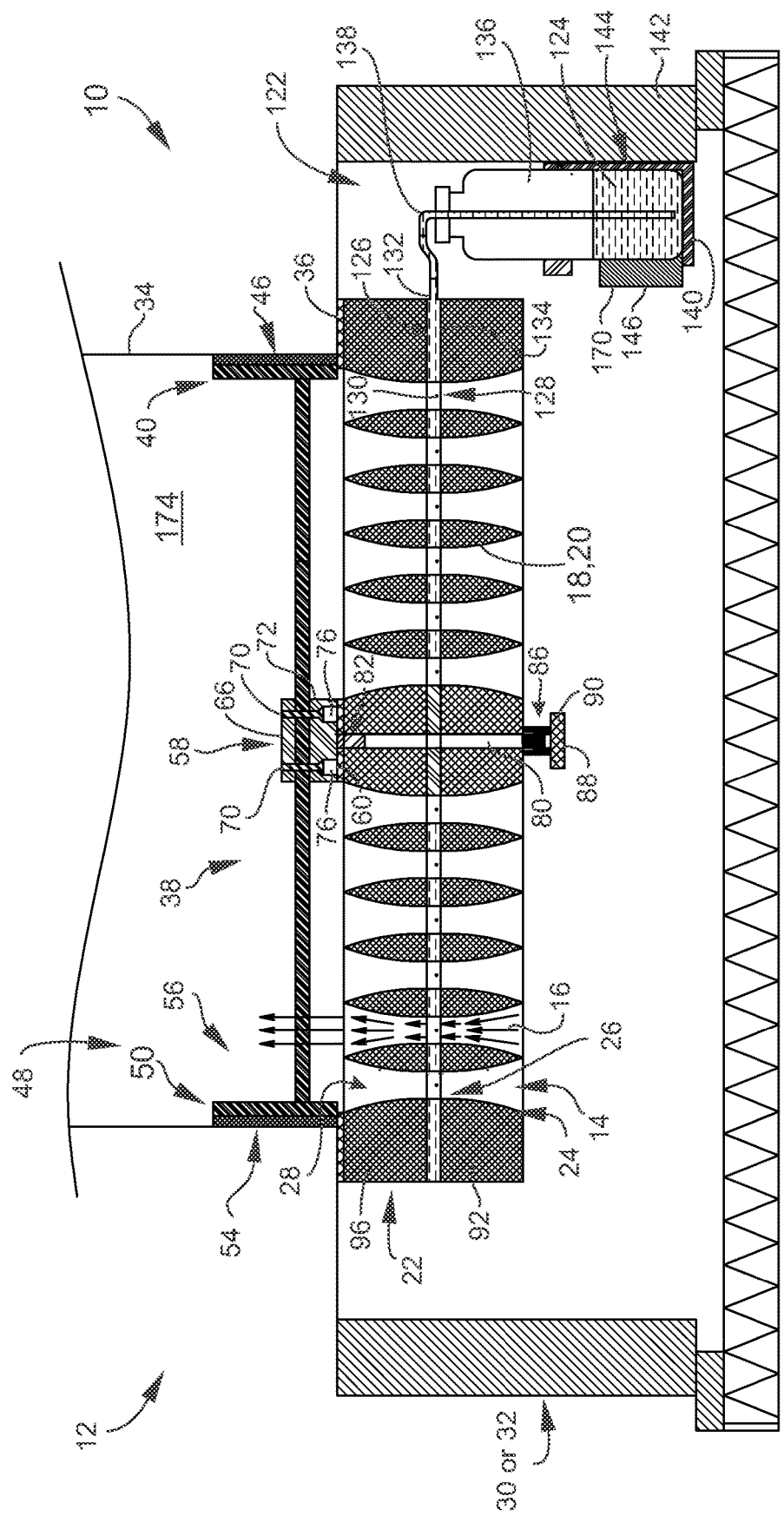
FIG. 22 shows a cross-sectional side view of the air decontamination apparatus for HVAC systems according to select embodiments of the instant disclosure installed into a common HVAC system with the antimicrobial liquid injection system.
Figure 23:
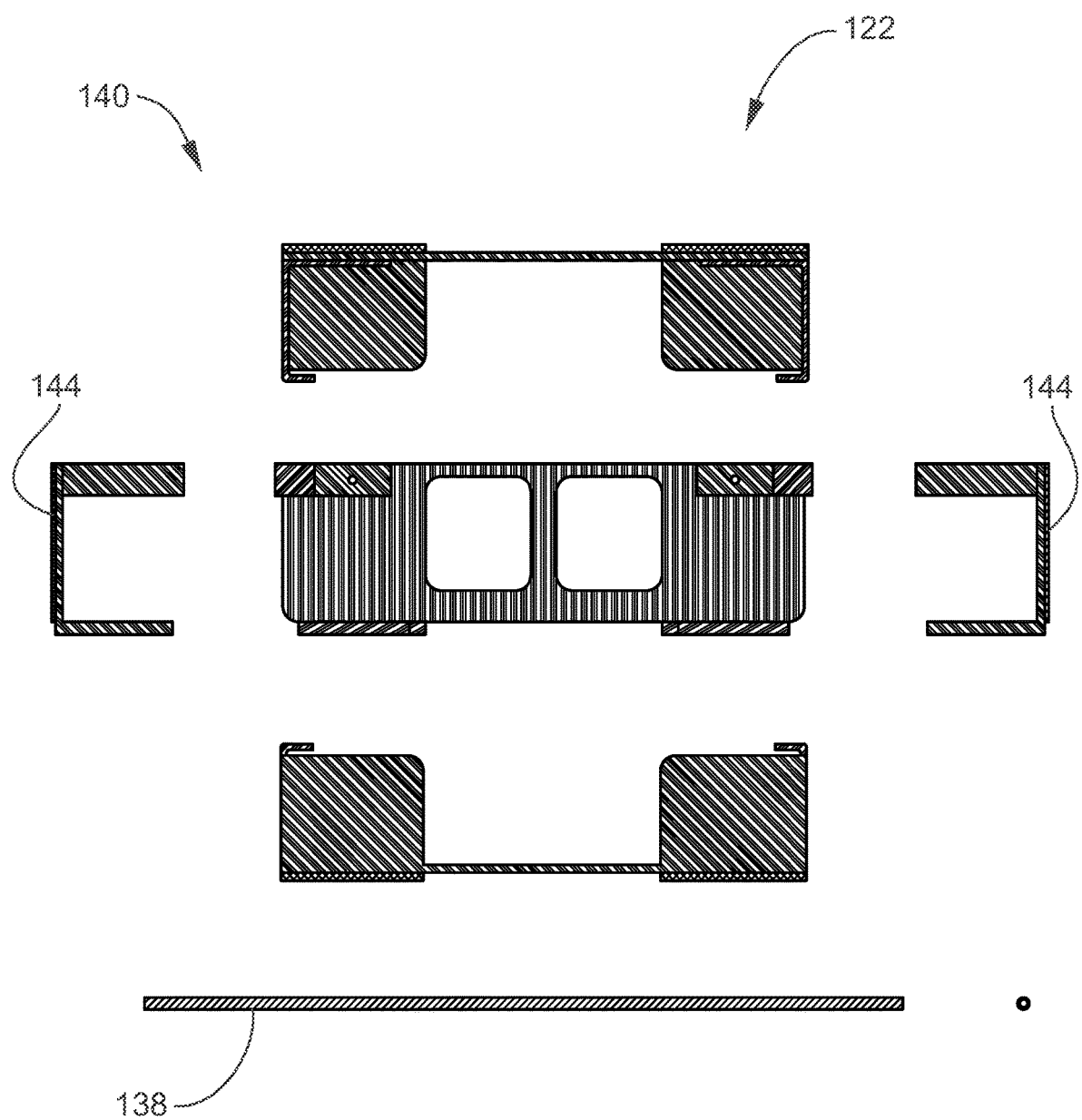
FIG. 23 shows a plurality of views of the reservoir mounting bracket for the antimicrobial liquid injection system according to select embodiments of the instant disclosure.
Figure 24:
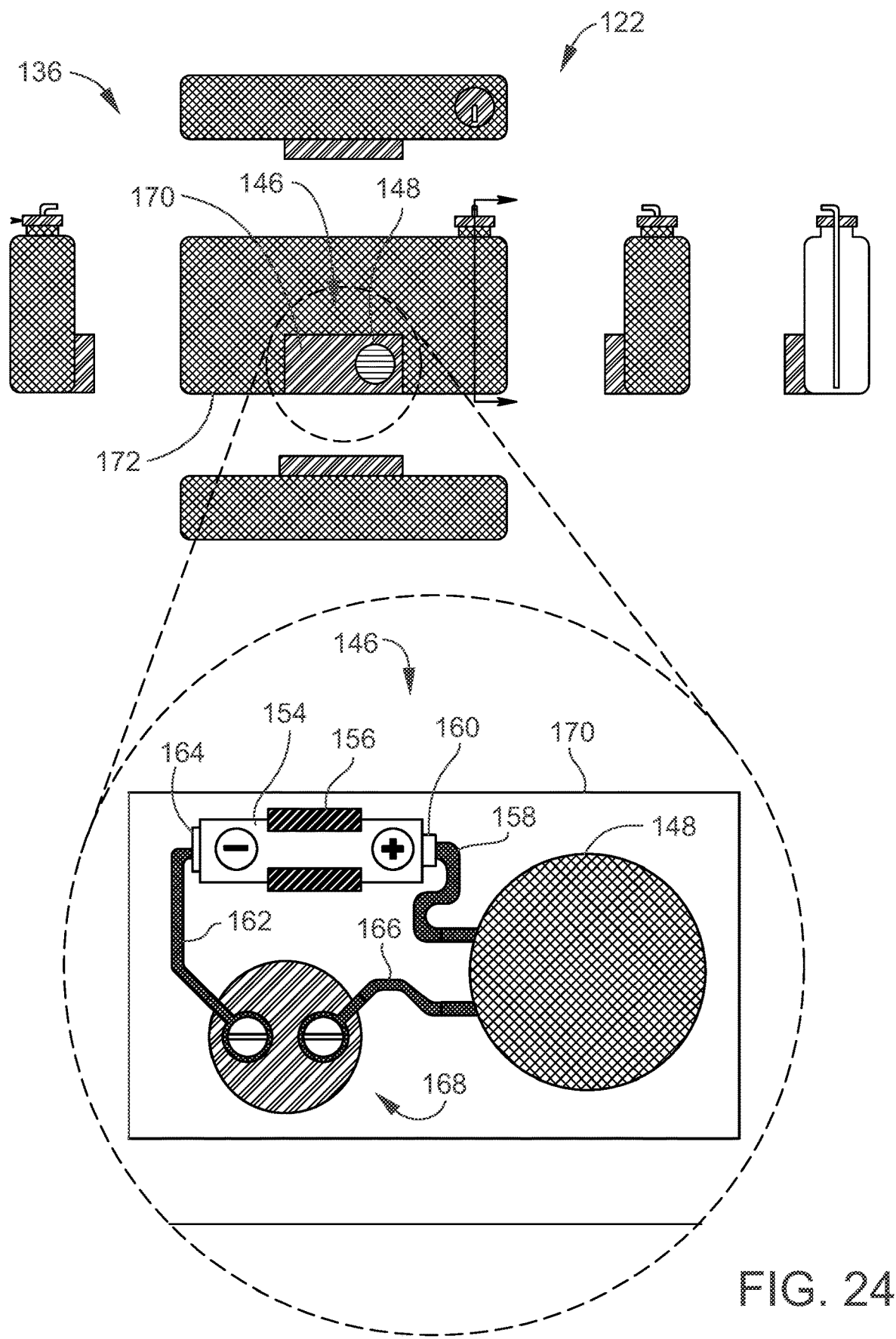
FIG. 24 shows a plurality of views of the reservoir for the antimicrobial liquid injection system according to select embodiments of the instant disclosure with a zoomed in view of the fluid level sensor showing a schematic diagram of the power supply for the fluid level sensor.

The present disclosure solves the aforementioned limitations of the currently available filtering or decontamination devices, apparatus, means and/or methods for filtering, removing, killing, decontaminating, the like, etc. any airborne bacterial micro-organisms and/or viruses in the air or environment of a common HVAC system, or the like, by providing air decontamination apparatus 10. Air decontamination apparatus 10 may be designed and/or configured for common HVAC system 12 (see FIGS. 11 and 22). Air decontamination apparatus 10 may generally include plurality of venturi holes 14. The plurality of venturi holes 14 may be configured to be positioned in common HVAC system 12 for forcing airflow 16 in common HVAC system 12 through the plurality of venturi holes 14, as best shown in FIGS. 11 and 22. At least each of the plurality of venturi holes 14 of air decontamination apparatus 10 may include antimicrobial coating 18. Wherein, air decontamination apparatus 10 may be configured to remove, kill, filter, decontaminate, the like, etc. any bacteria and viruses in airflow 16 in common HVAC system 12, or the like, via antimicrobial coating 18 on at least each of the plurality of venturi holes 14.

One feature of the disclosed air decontamination apparatus for HVAC systems may be that antimicrobial coating 18 can be electrostatic antimicrobial coating 20. Electrostatic antimicrobial coating 20 may be applied to all surfaces of air decontamination apparatus 10, including, but not limited to, all portions of each of the plurality of venturi holes 14.

Figure 12:
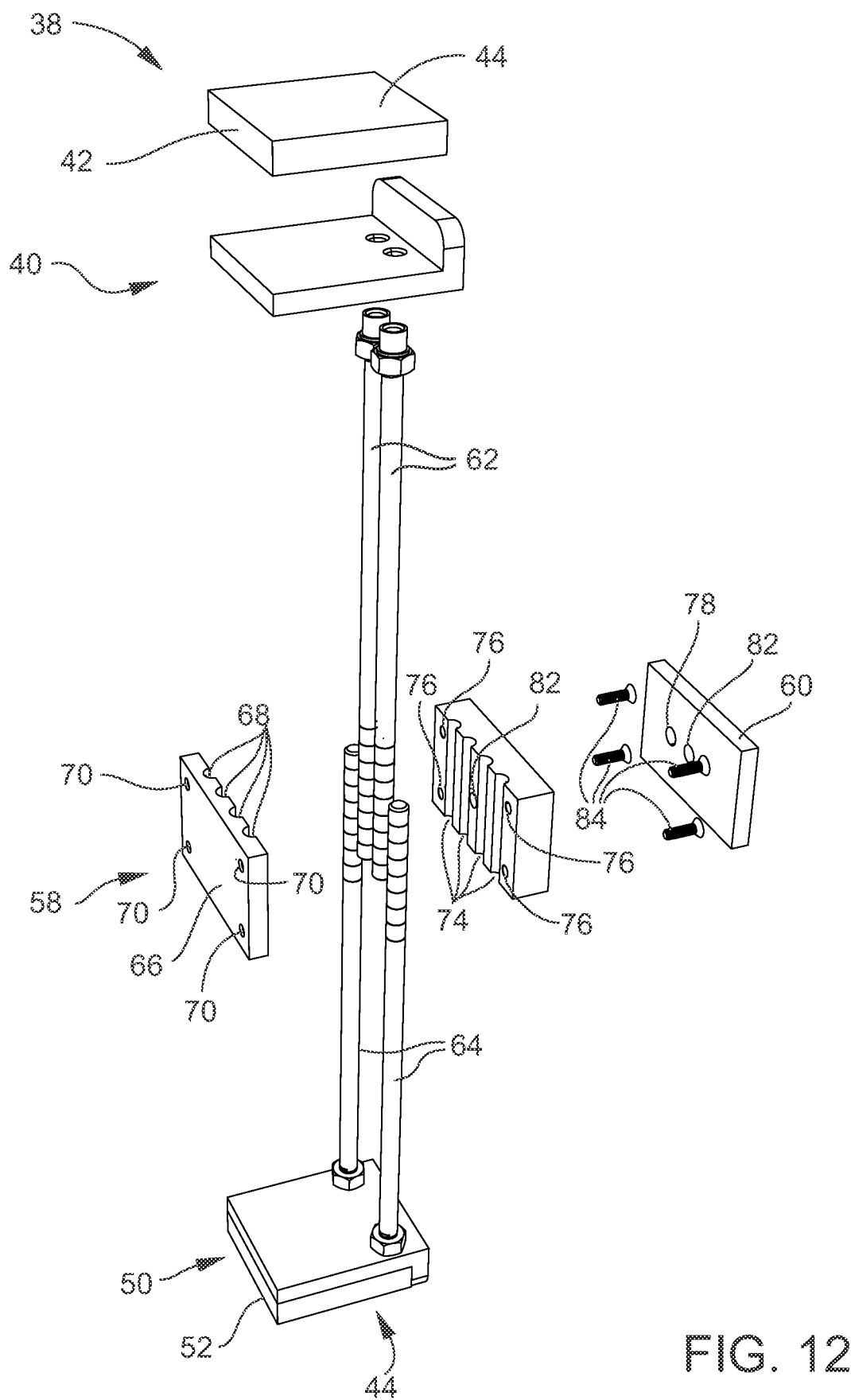
FIG. 12 shows an exploded view of the mounting bracket assembly for the air decontamination apparatus for HVAC systems according to select embodiments of the instant disclosure.
Figure 13:
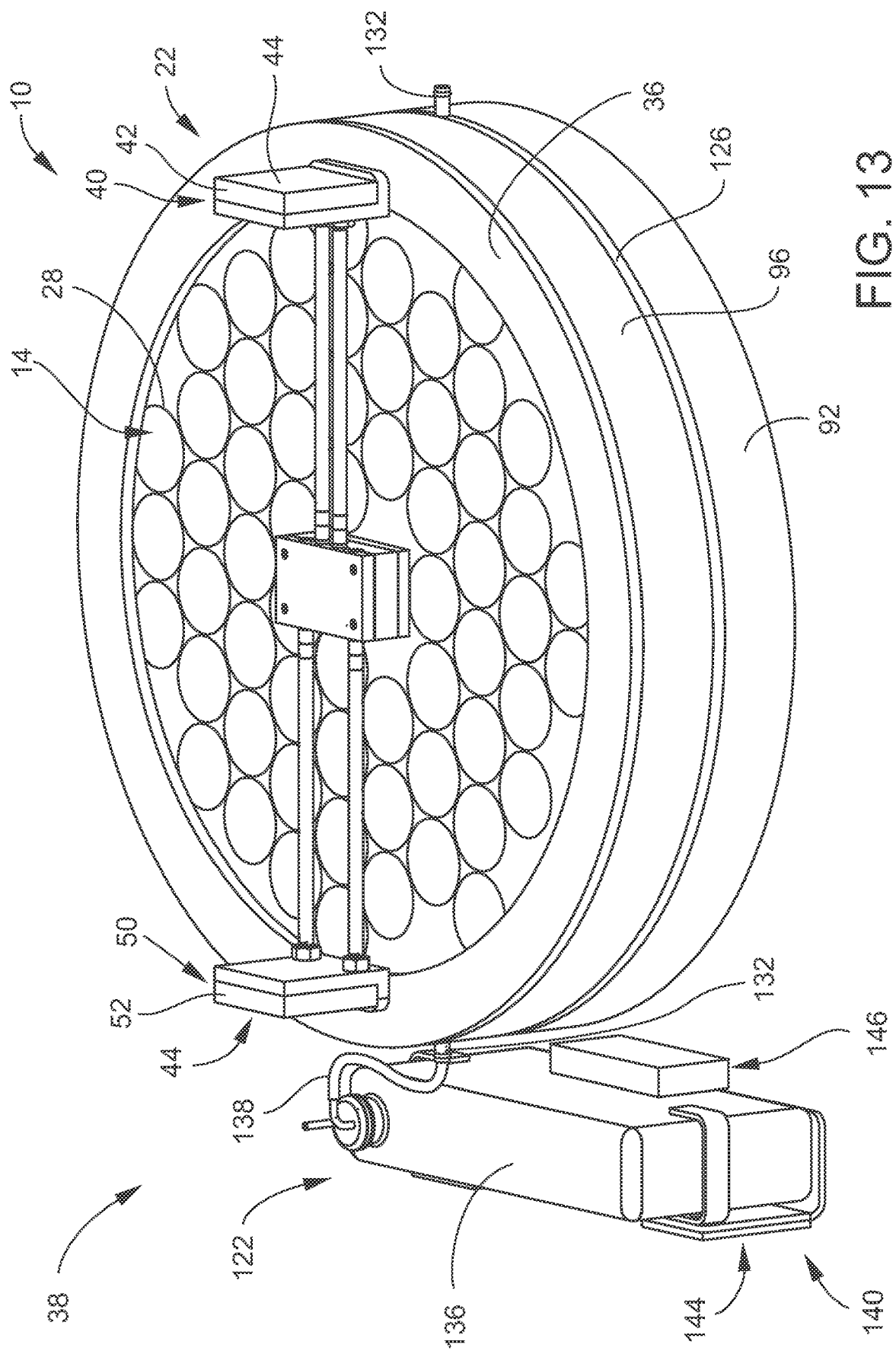
FIG. 13 shows a top perspective view of an air decontamination apparatus for HVAC systems according to select embodiments of the instant disclosure with an antimicrobial liquid injection system with an antimicrobial liquid injection system.
Figure 14:
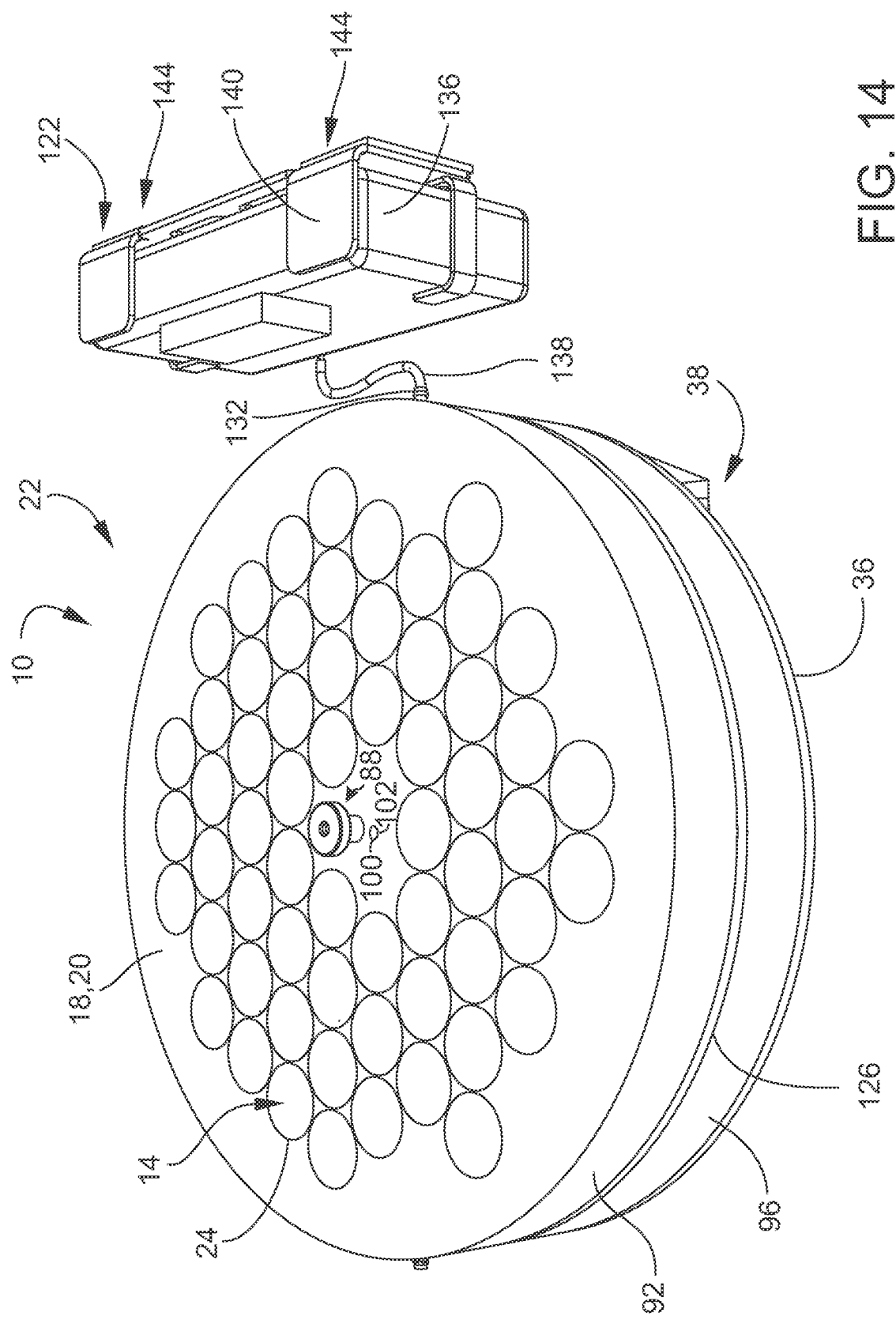
FIG. 14 shows a bottom perspective view of the air decontamination apparatus for HVAC systems of FIG. 13 with the antimicrobial liquid injection system.
Figure 15:
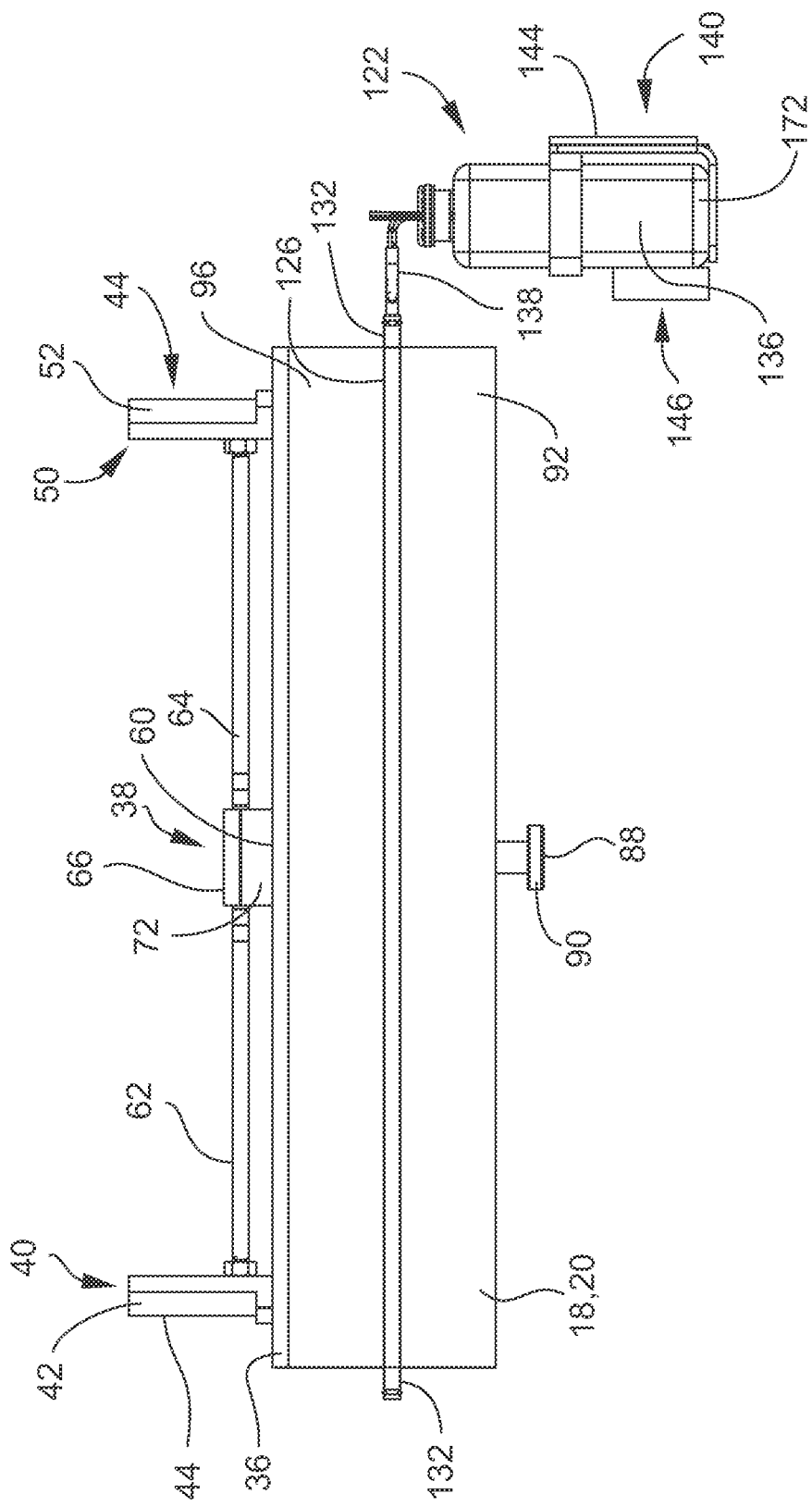
FIG. 15 shows a side view of the air decontamination apparatus for HVAC systems of FIG. 13 with the antimicrobial liquid injection system.
Figure 16:
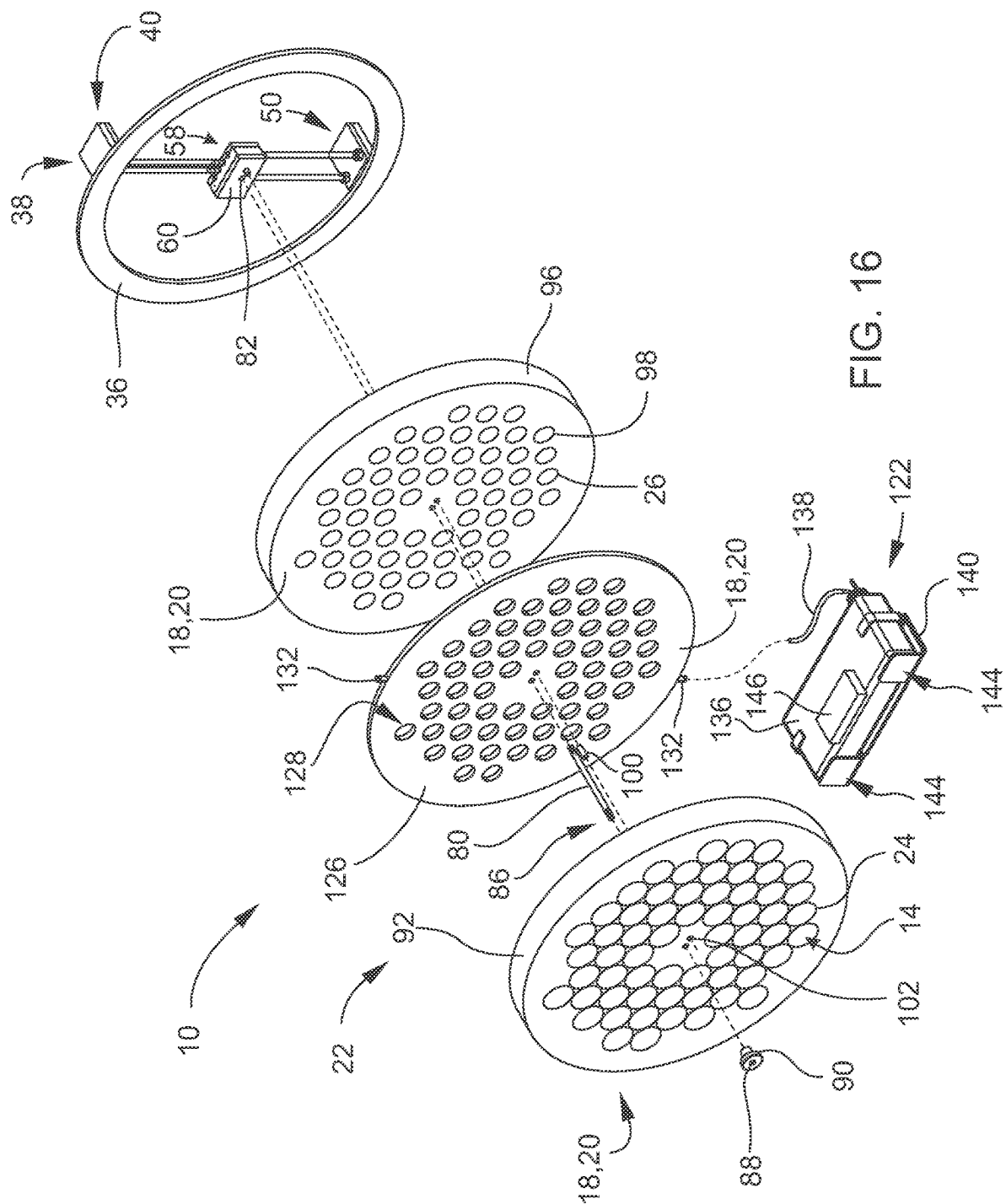
FIG. 16 shows a partially disassembled bottom perspective view of the air decontamination apparatus for HVAC systems of FIG. 13 with the antimicrobial liquid injection system.
Figure 17:
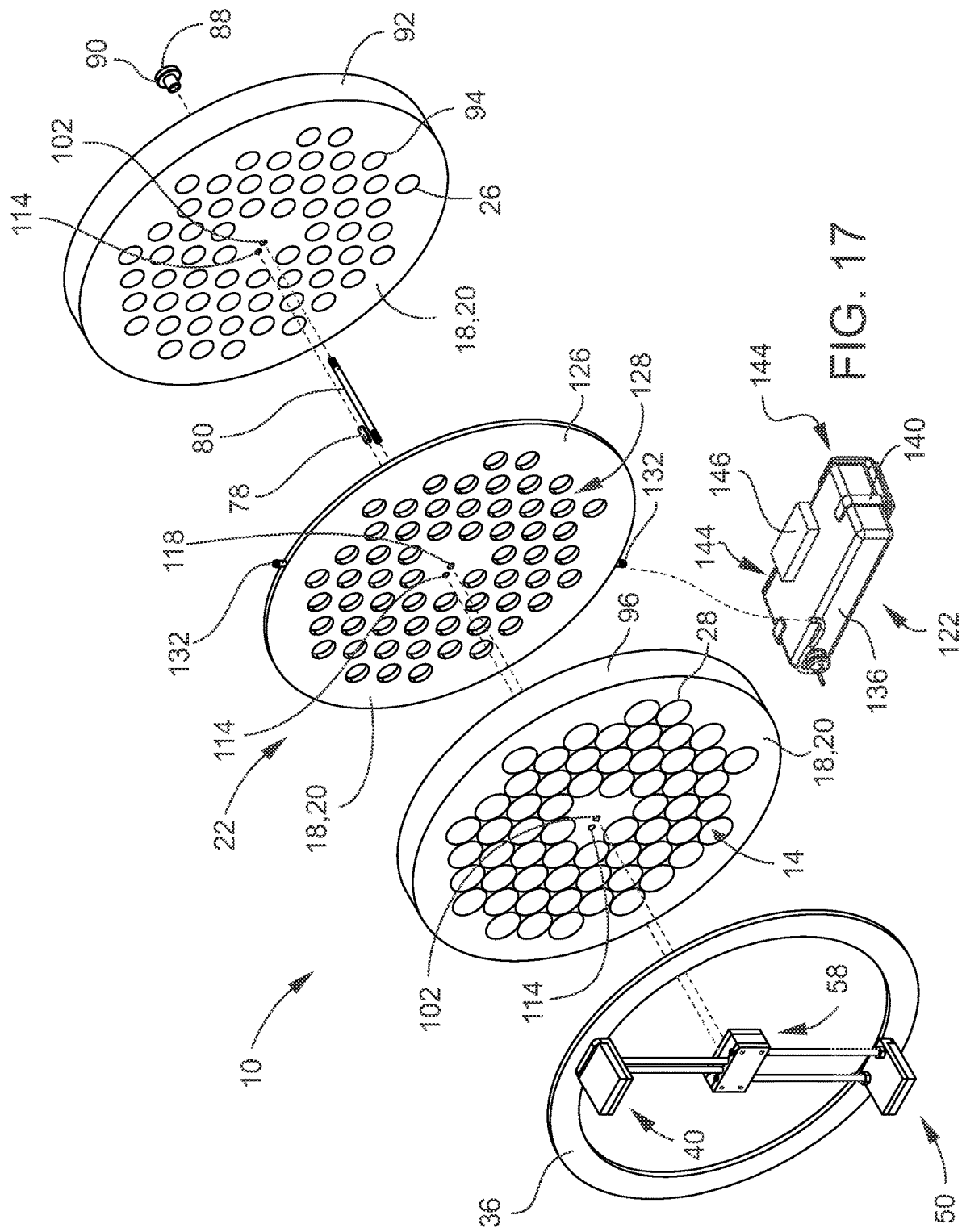
FIG. 17 shows a partially disassembled top perspective view of the air decontamination apparatus for HVAC systems of FIG. 13 with the antimicrobial liquid injection system.
Figure 18:
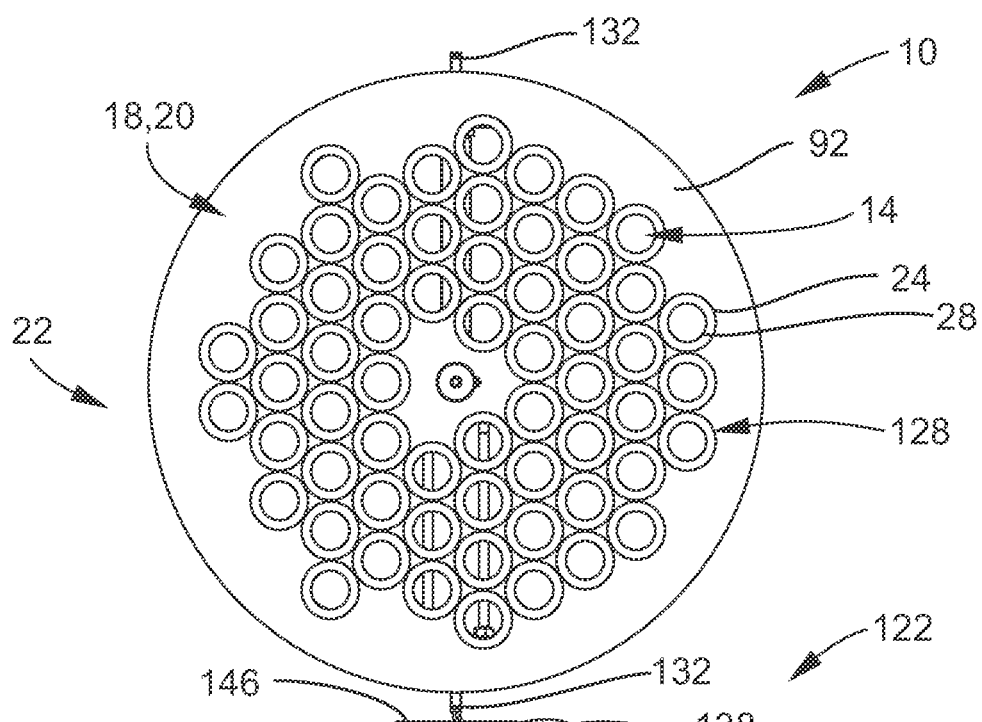
FIG. 18 shows a front view of the air decontamination apparatus for HVAC systems of FIG. 13 with the antimicrobial liquid injection system.
Figure 19:
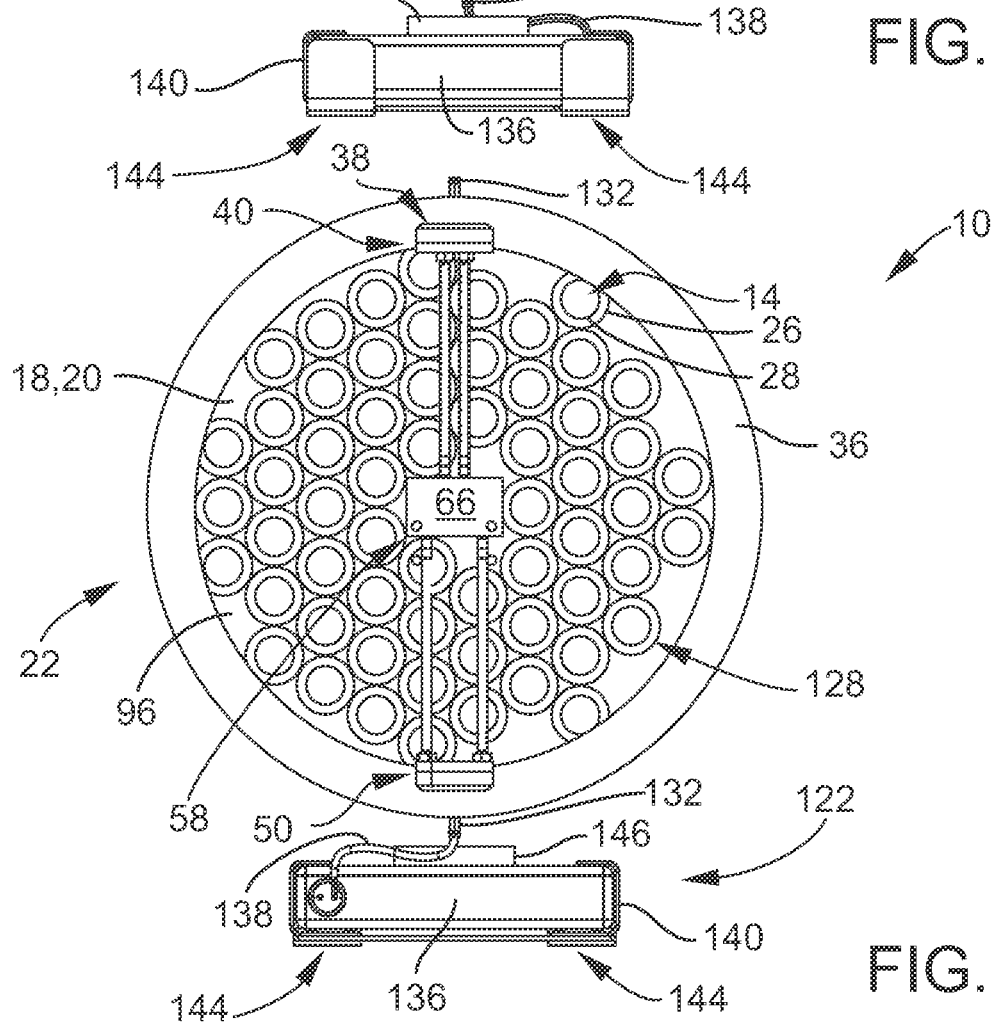
FIG. 19 shows a rear view of the air decontamination apparatus for HVAC systems of FIG. 13 with the antimicrobial liquid injection system.
Figure 21:
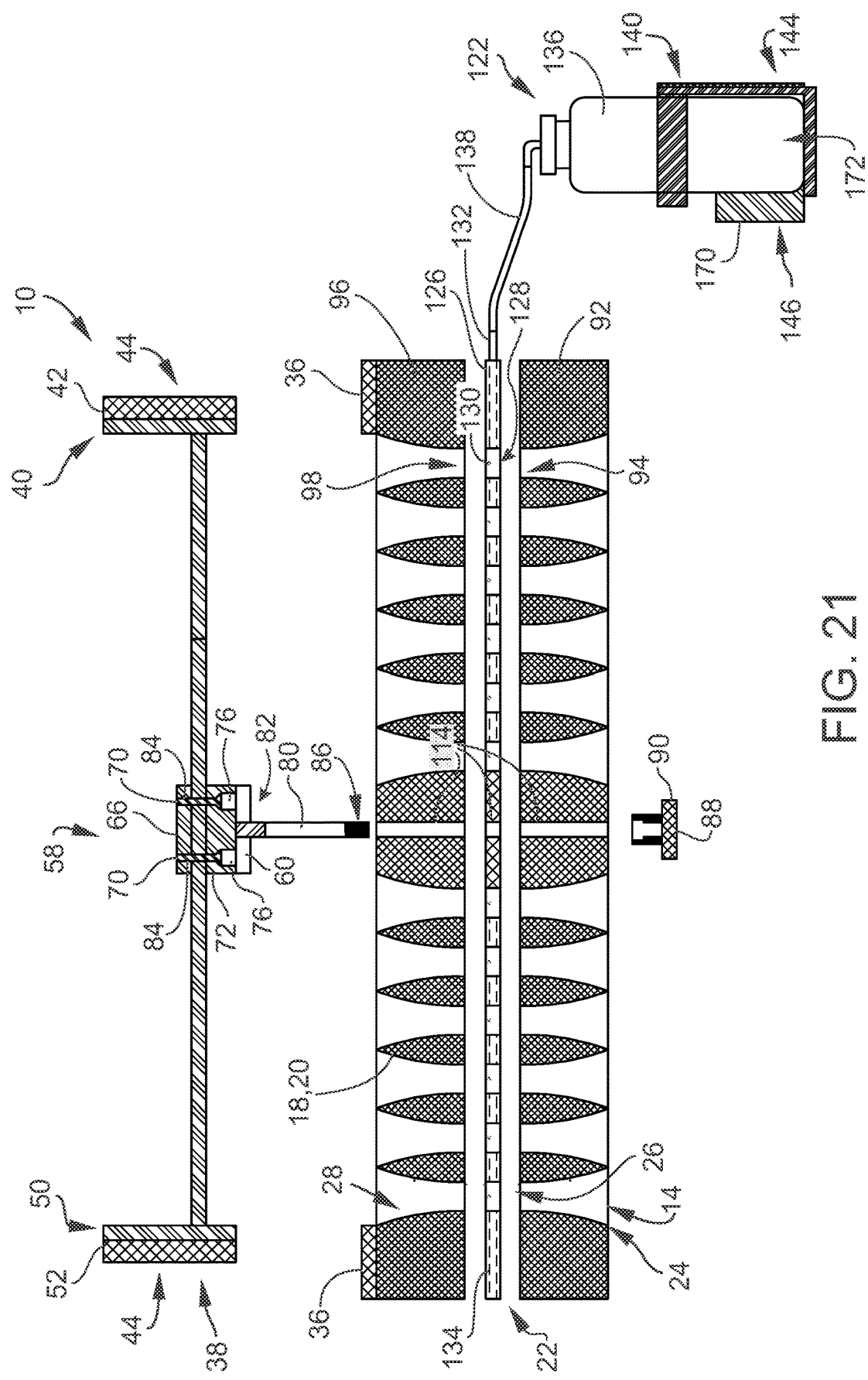
FIG. 21 shows a cross-sectional side view of the air decontamination apparatus for HVAC systems of FIG. 13 with the antimicrobial liquid injection system.

Venturi plate device 22 may be included in select embodiments of air decontamination apparatus 10 for HVAC systems 12. See FIGS. 1-7, 10-11, 13-19, and 21-22. Venturi plate device 22 may be designed and configured to include plurality of venturi holes 14 for positioning each of the plurality of venturi holes 14 in airflow 16 of common HVAC system 12, or the like. Each of the plurality of venturi holes 14 in venturi plate device 22 may include wide inlet portion 24, narrow middle portion 26, and wide exhaust portion 28, as best shown in the cross-sectional views of 7, 10, 11, 21 and 22. Where, wide inlet portion 24 of each venturi hole 14 tapers into narrow middle portion 26 and narrow middle portion 26 tapers out to wide exhaust portion 28. As best shown in FIGS. 11 and 12, venturi plate device 22 may be configured to be sealed between inlet 30 of common HVAC system 12, or outlet 32 of common HVAC system 12 for forcing airflow 16 of common HVAC system 12 through each of the plurality of venturi holes 14 in venturi plate device 22. As such, venturi plate device 22 may be sized and configured to be sealed to duct 34 of common HVAC system 12 in inlet 30 or outlet 32 of common HVAC system 12. In select embodiments, venturi plate device 22 may be sealed to duct 34 of common HVAC system 12 in inlet 30 or outlet 32 of common HVAC system 12 via foam seal 36 around venturi plate device 22. Foam seal 36 may be any device or means for sealing venturi plate device 22 to duct 34, including, but not limited to, being a foam seal.

Referring now specifically to FIG. 12, another feature of air decontamination apparatus 10 for HVAC systems 12 may be the inclusion of mounting bracket 38. Mounting bracket 38 may be designed and/or configured to secure venturi plate device 22 to be sealed between inlet 30 of common HVAC system 12 or the outlet 32 of common HVAC system 12. As best shown in FIGS. 11 and 22, in select embodiments, mounting bracket 38 may be configured to be mounted inside duct 34 of common HVAC system 12 for sealing venturi plate device 22 to duct 34 and positioning venturi plate device 22 in airflow 16. In select embodiments, mounting bracket 38 may include upper mount 40, lower mount 50, adjustable rod bracket 58, and mounting plate 60. Upper mount 40 may have upper foam pad 42. Upper foam pad 42 can include adhesive 44 configured to secure upper mount 40 to first portion 46 of inside 48 of duct 34. Likewise, lower mount 50 may have lower foam pad 52. Lower foam pad 52 can include the same adhesive 44 configured to secure lower mount 50 to second portion 54 of inside 48 of duct 34. Second portion 54 may be on opposite side 56 of duct 34 from first portion 46 on inside 48 of duct 34. Adjustable rod bracket 58 may be connected between upper mount 40 and lower mount 50. Mounting plate 60 may be connected to adjustable rod bracket 58. Mounting plate 60 may be configured to secure venturi plate device 22 to adjustable rod bracket 58 connected between upper mount 40 and lower mount 50.

As shown in FIG. 12, in select embodiments, adjustable rod bracket 58 can include pair of inner rods 62 and pair of outer rods 64. Pair of inner rods 62 may be connected to upper mount 40, and pair of outer rods 64 may be connected to lower mount 50 (or vice versa). In this embodiment, mounting plate 60 may include upper clamp plate 66 and lower clamp plate 72. Upper clamp plate 66 can include four upper half-round cuts 68 and plurality of threaded holes 70 (i.e., 4 threaded holes 70). Lower clamp plate 72 can include four lower half-round cuts 74 configured to mirror the four upper half-round cuts 68, and a plurality of counterbore holes 76 (i.e., 4 counterbore holes 76) configured to align with the plurality of threaded holes 70 in upper clamp plate 66. Mounting alignment dowel 78 may protrude from lower clamp plate 72. Mounting stud 80 may be secured to lower clamp plate 72 through center hole 82 in lower clamp plate 72. Wherein, mounting plate 60 may be configured to be adjustably secured to the pair of inner rods 62 and the pair of outer rods 63 via the lower clamp plate 72 being secured to the upper clamp plate 66 and squeezed around the pair of inner rods 62 and the pair of outer rods 64 in between the four upper half-round cuts 68 and the four lower half-round cuts 74 via plurality of screws 84 connected between the plurality of threaded holes 70 in the upper clamp plate 66 and the plurality of counterbore holes 76 in the lower clamp plate 72. In select embodiments, mounting stud 80 may be configured to connect venturi plate device 22 to mounting plate 60 via threaded connection 86 to knob 88. In select embodiments, knob 88 may include knurled outer diameter 90, as shown in the Figures. In other select embodiments, mounting alignment dowel 78 may be configured to align venturi plate device 22 about mounting plate 60 via alignment hole 102 in venturi plate device 22.

As best shown in the disassembled exploded view of FIGS. 4, 5, 16 and 17, in select embodiments of air decontamination apparatus 10 for HVAC systems 12, or the like, venturi plate device 22 may include inlet venturi plate 92 and exhaust venturi plate 96. See FIGS. 8A-8D. Inlet venturi plate 92 may include wide inlet portion 24 of each of the plurality of venturi holes 14 and narrow inlet portion 94 of narrow middle portion 26 of each of the plurality of venturi holes 14. Exhaust venturi plate 96 may have wide exhaust portion 28 of each of the plurality of venturi holes 14 and narrow exhaust portion 98 of the narrow middle portion 26 of each of the plurality of venturi holes 14. Narrow inlet portions 94 of each of the narrow middle portions 26 in inlet venturi plate 92 may be aligned and fluidly connected to narrow exhaust portions 98 of each of the narrow middle portions 26 of exhaust venturi plate 96. In select embodiments, plate alignment dowel 100 may be included. Plate alignment dowel 100 may protrude from inlet venturi plate 92 and into alignment hole 102 of exhaust venturi plate 96, or vice versa. Plate alignment dowel 100 may be configured to align each of the plurality of narrow inlet portions 94 in the inlet venturi plate 92 with each of the narrow exhaust portions 98 in the exhaust venturi plate 96 for creating the plurality of venturi holes 14 therebetween. In select embodiments, inlet venturi plate 92 and exhaust venturi plate 96 may be completely coated with antimicrobial coating 18, like electrostatic antimicrobial coating 20. This 2-piece construction and design of venturi plate device 22 with separate inlet venturi plate 92 and exhaust venturi plate 96 may allow for more complete and uniform application of antimicrobial coating 18, like electrostatic antimicrobial coating 20.

Referring now specifically to the embodiments shown in FIGS. 1-11, one feature of air decontamination apparatus 10 for HVAC systems 12 may be the inclusion of intermediate antimicrobial plate 104. See FIGS. 9A-9D. Intermediate antimicrobial plate 104 may be positioned between inlet venturi plate 92 and exhaust venturi plate 96. Intermediate antimicrobial plate 104 may be designed and configured to circulate or swirl airflow 16 moving through venturi holes 14 for providing more contact of airflow 16 with antimicrobial coating 18. As best shown in FIGS. 9A-9D, intermediate antimicrobial plate 104 may include a plurality of bladed holes 106. Plurality of bladed holes 106 may be configured to be positioned between narrow inlet portions 94 in inlet venturi plate 92 and narrow exhaust portions 98 in exhaust venturi plate 96. In select embodiments, as shown best in FIGS. 9C and 9D, each of the plurality of bladed holes 106 may include plurality of turbulence blades 108. Each turbulence blade 108 may include sharp inlet edge 110 angled toward wider exit edge 112. See FIG. 9D. Each turbulence blade 108 of each of the plurality of bladed holes 106 may include antimicrobial coating 18, like electrostatic antimicrobial coating 20. Wherein, intermediate antimicrobial plate 104 may be designed and/or configured to swirl airflow 16 through the plurality of venturi holes 14. In select embodiments, intermediate antimicrobial plate 104 may further include center through hole 114 configured to receive mounting stud 80 therethrough. Intermediate alignment hole 118 may also be included that is configured to receive plate alignment dowel 100 therethrough, thereby aligning plurality of bladed holes 106 between narrow inlet portions 94 in inlet venturi plate 92 and narrow exhaust portions 98 in exhaust venturi plate 96. The entire intermediate antimicrobial plate 104 may include antimicrobial coating 18. In select embodiments, as best shown in FIG. 8C, each of the plurality of bladed holes 106 may include eight turbulence blades 108 equally spaced for creating fan design 120.

Referring now to FIGS. 13-24, another feature of air decontamination apparatus 10 for HVAC systems 12 may be the inclusion of antimicrobial liquid injection system 122. Antimicrobial liquid injection system 122 may be configured to insert antimicrobial liquid 124 into airflow 16 moving through each of the venturi holes 14 of venturi plate device 22. Antimicrobial liquid injection system 122 may optionally be used in place of intermediate antimicrobial plate 104, as shown in the Figures, or in combination with intermediate antimicrobial plate 104. In select embodiments, antimicrobial liquid injection system 122 may include liquid intermediate plate 126. See FIG. 20A-20E. Liquid intermediate plate 126 may be positioned between inlet venturi plate 92 and exhaust venturi plate 96. In select embodiments, liquid intermediate plate 126 may include plurality of injection holes 128 configured to be positioned between narrow inlet portions 94 in inlet venturi plate 92 and narrow exhaust portions 98 in exhaust venturi plate 96. Each of the plurality of injection holes 128 may include at least one fluid port 130. Wherein, liquid intermediate plate 126 may be configured to insert antimicrobial liquid 124 into airflow 16 through the plurality of venturi holes 14 via the at least one fluid port 130 in each of the plurality of injection holes 128. In select embodiments, liquid intermediate plate 126 may further include at least one hose port 132 configured to communicate with hollow interior 134 of liquid intermediate plate 126. Hollow interior 134 of liquid intermediate plate 126 may fluidly connect each of the at least one hose ports 132 with each of the fluid ports 130 in each of the plurality of injection holes 128. See FIG. 20E. In other select embodiments of liquid intermediate plate 126, center through hole 114 may be included that may be configured to receive mounting stud 80. In other select embodiments of liquid intermediate plate 126, intermediate alignment hole 118 may be included that can be configured to receive plate alignment dowel 100 therethrough, thereby aligning the plurality of injection holes 128 between narrow inlet portions 94 in inlet venturi plate 92 and narrow exhaust portions 98 in exhaust venturi plate 96. In select embodiments, the entire liquid intermediate plate 126 may include antimicrobial coating 18, like electrostatic antimicrobial coating 20. In select embodiments, each of the plurality of injection holes 128 may include four fluid ports 130 equally spaced around the injection hole 128, and each of the plurality of injection holes 128 may be angled from wide inlet portions 24 toward the wide exhaust portions 28 of the venturi holes 14. See FIG. 20D.

Reservoir 136 may be included in select embodiments of antimicrobial liquid injection system 122. See FIGS. 13-19, 21-22, and 24. Reservoir 136 may be for storing antimicrobial liquid 124 for antimicrobial liquid injection system 122 of air decontamination apparatus 10. In these embodiments, antimicrobial liquid injection system 122 may include reservoir 136 with hose 138 and reservoir mounting bracket 140. Hose 138 (see bottom view of FIG. 23 may be connected between reservoir 136 and the at least one hose port 132 of liquid intermediate plate 126. Hose 138 may include multiple hoses or connections for connecting to multiple hose ports 132 on liquid intermediate plate 126. Reservoir mounting bracket 140 may be configured to hold reservoir 136 and be mounted to the inside of filter housing 142 of common HVAC system 12 via adhesive strips 144. See FIG. 22. In select embodiments, antimicrobial liquid injection system 122 may further include fluid level sensor 146 in reservoir 136. Fluid level sensor 146 may be configured to sense the amount of antimicrobial liquid 124 inside of reservoir 136. In select embodiments, buzzer 148 may also be included. Buzzer 148 may be in communication with fluid level sensor 146. Buzzer 148 may be configured to emit an alarm sound when fluid level sensor 146 senses the amount of the antimicrobial liquid 124 inside of reservoir 136 is below a set refill amount. In select embodiments of antimicrobial liquid injection system 122, battery 154 may be included that can be configured to power buzzer 148 and/or fluid level sensor 146. Battery 154 may be mounted on reservoir 136 via battery holder 156. As best shown in the zoomed in schematic view of FIG. 24, positive connector wire 158 may be connected between positive side 160 of battery 154 and buzzer 148. First negative connector wire 162 may be connected between negative side 164 of battery 154 and fluid level sensor 146. Second negative connector wire 166 may be connected between fluid level sensor 146 and buzzer 148. With this configuration, fluid level sensor 146 may be normally closed fluid activated sensor 168 configured to close when dry and open when wet. Low fluid level warning kit cover 170 may be attached to bottom 172 of reservoir 136 configured to house and seal battery 154, buzzer 148, and fluid level sensor 146.

One feature of antimicrobial liquid injection system 122 for air decontamination apparatus 10 for HVAC systems 12 may be that antimicrobial liquid injection system 122 may be configured to allow antimicrobial liquid 124 to be drawn out of each of the fluid ports 130 in each of the injection holes 128 via low pressure 174 created by airflow 16 of common HVAC system 12, or the like.

In another aspect, the instant disclosure embraces air decontamination apparatus 10 for HVAC system 12, or the like, in any of the embodiments and/or combination of embodiments shown and/or described herein.

In another aspect, the instant disclosure embraces air decontamination apparatus 10 for HVAC system 12, or the like, with intermediate antimicrobial plate 104 in any of the embodiments and/or combination of embodiments shown and/or described herein, like as shown in FIGS. 1-11.

In another aspect, the instant disclosure embraces air decontamination apparatus 10 for HVAC system 12 with antimicrobial liquid injection system 122 in any of the embodiments and/or combination of embodiments shown and/or described herein, like as shown in FIG. 13-24.

In sum, the instant disclosure is designed to provide air decontamination apparatus 10 with a means of killing virus and bacterial micro-organisms in airflow 16 entering (or leaving) an HVAC system, including, but not limited thereto, common HVAC system 12 shown herein. Air decontamination apparatus 10 may provide two means of accomplishing this, either a chemical free antimicrobial coating method to kill bacteria and viruses (with or without intermediate antimicrobial plate 104), or the addition of antimicrobial liquid injection system 122 to the same system that uses the release of an antibacterial, virucide chemical (i.e., antimicrobial liquid 124) by means of a venturi, with no electronics required. This antimicrobial liquid injection system 122 may draw an inhalation safe chemical into the airstream (airflow 16) that can be introduced into the inlet air to be circulated throughout HVAC system 12. This system can be utilized either on inlet 30 of the air system, or the exit 32 of the air system into the room. For the non-chemical means, an electrostatically charged antimicrobial coating 20 may be applied to inlet venturi plate 92, intermediate antimicrobial plate 104, and exhaust venturi plate 96 that forces the air to travel over these coated surfaces. At the cellular level, this contact kills the single cell organism, preventing its introduction and recirculation into HVAC system 12, and thus preventing the spread of the bacteria or virus into other rooms connected to the system. For the addition of an inhalation approved antibacterial or virucide, intermediate antimicrobial plate 104 may be changed out (or added to) from venturi plate device 22 of air decontamination apparatus 10 with liquid intermediate plate 126. Liquid intermediate plate 126 may be positioned at the center or low-pressure area of each venturi hole 14. Liquid intermediate plate 126 may have small fluid ports 130 that release antimicrobial liquid 124, drawn by low pressure 174 area into the airstream. When the HVAC blower turns off and the airflow stops, the flow of antimicrobial liquid 124 may stop until the next time the HVAC system turns on.

One feature or advantage of the disclosed air decontamination apparatus 10 may be that it can easily install into the inlet side of an HVAC system by removing the standard air filter, installing mounting bracket 38 into the ductwork, installing the three plates, and then reinstalling the standard air filter. No modifications may be required to the ductwork or any of the original items on the HVAC system.

Another feature or advantage of the disclosed air decontamination apparatus 10 may be that it can be removed easily, and may be completely transferrable to a new home, leaving no trace of its installation.

Another feature or advantage of the disclosed air decontamination apparatus 10 may be that with use of intermediate antimicrobial plate 104, no chemical inhalation hazards are present, so there may be no risks or regulations from a health regulation or allergy standpoint, where the virus may be killed by contact with the antimicrobial electrostatic surfaces. No chemical agent may be released into the ductwork that will be inhaled by the occupants of the home or business. In addition, no electronics required for this configuration at all.

Another feature or advantage of the disclosed air decontamination apparatus 10 may be, for embodiments with antimicrobial liquid injection system 122, these embodiments may allow the introduction of a specific chemical to target a specific virus or bacteria. Antimicrobial liquid 124 can be refilled or replaced without removal of any of the plates or system in the ductwork, still easily accessible in the plenum above the air filter. Low fluid level sensor 146 may activate buzzer 148 when reservoir 136 needs to be refilled.

The antimicrobial method in which the disclosed air decontamination apparatus 10 may kill the virus or bacteria is not as specific as a chemical agent to one virus or bacteria strain, thus making the antimicrobial coated method a more universal air purification for all types or airborne threats in the future.

Another feature or advantage of the disclosed air decontamination apparatus 10 may be the inclusion of the two-piece venturi design with inlet venturi plate 92 and exhaust venturi plate 96. This two-piece design may allow the plurality of venturi holes 14 to be coated more uniformly from both sides when being electrostatically coated with the antimicrobial coating. As a result, a better coverage of the coating is possible. In addition, this two-piece venturi design may allow for easy cleaning and recoating, as the coating must remain free from dirt and debris to be effective. The location of air decontamination apparatus 10 directly above the standard inlet filter of the home, allows for the cleanest air to be run through the venturis, which may prolong the effectiveness of coating 18, like electrostatic coating 20, before needing to be cleaned.

Another feature or advantage of the disclosed air decontamination apparatus 10 may be that system maintenance can easily be carried out. The plates of venturi plate device can be removed, cleaned and reinstalled completely toolless, by removing capture knob 88 off mounting stud 80 and then sliding the plates off the mounting stud 80, leaving mounting bracket 38 completely installed, and allowing for complete removal of the plates for cleaning.

Another feature or advantage of the disclosed air decontamination apparatus 10 may be to provide an adaptable design concept for all sizes of ductwork and air inlet sizes by changing the number of venturi holes 14. The venturi pattern can be made to fit any size of inlet ducting, including the size and shape of venturi plate device 22.

Another feature or advantage of the disclosed air decontamination apparatus 10 may be that no electronic components maybe required in either system for the air to be purified. The only no batteries or wiring in the system may be for the low fluid level sensor 146. The system functions off the HVAC system airflow 16, whereby when airflow 16 stops, the treatment stops, even the flow of the chemical that is induced by the low pressure area 174 in the venturi holes 14 also stops when the air flow stops. No switches or connection may be required into the existing HVAC electrical system or thermostat.

Another feature or advantage of the disclosed air decontamination apparatus 10 may be that it can use all the same base mounting components for both styles of airborne contaminant elimination, the difference for antimicrobial liquid injection system 122 may be the removal of intermediate antimicrobial plate 104 and replacing it with liquid intermediate plate 126 and all of the other components of liquid injection system 122 with reservoir 136. Inlet venturi plate 92 and exhaust venturi plate 96 may be completely interchangeable to use for either style of system.

Another feature or advantage of the disclosed air decontamination apparatus 10 may be the use of a venturi design, incorporated with an electrostatic antimicrobial coating on the contact surfaces, that at a microscopic level, uses "swords" to cut or puncture the outer skin of the virus. The method of compressing the air flow into venturi holes 14, and then impacting that air on either the blade surface, or by treating the air with an additional antibacterial as it passes through the venturi holes 14 is the basis for air decontamination apparatus 10. As the blower motor turns on in HVAC system 12, low pressure area 174 is created in the ductwork, which causes air to flow through the filter and into the venturi holes 14. As the air enters the venturis, it is forced to speed up at the center of the venturis.

Another feature or advantage of the disclosed air decontamination apparatus 10 may be that in the embodiments without the antimicrobial liquid injection system 122, the air stream is forced and focused into the blade area (intermediate antimicrobial plate 104) of the venturi holes 14. The additional surface area of the turbulence blades 108 and the angle they are at, forces the air stream over the antimicrobial surface, and also creates turbulence that pushes the air stream out against the sides of the wide exhaust portion 28 of the venturi holes 14. This pushing and focusing of the air on these surfaces helps to eliminate airborne micro bacteria and viruses, thereby purifying the air that is being distributed throughout the entire HVAC system. With this system there are no chemicals to inject into the air, just the air flow over the treated surfaces to kill the bacteria and virus. This method of purification does not require any modification to the existing HVAC system 12 or components of that system.

Another feature or advantage of the disclosed air decontamination apparatus 10 may be that in the embodiments with the antimicrobial liquid injection system 122, as the air flows into wide inlet portion 24 of inlet venturi plate 92, it speeds up through the restricted opening, this creates a low-pressure area in the center of the venturi holes 14. Liquid intermediate plate 126 is a hollow plate with fluid passages all around the port areas that are exposed to the low-pressure area created in the center of the venturi holes 14. This fluid area is connected to reservoir 136, by way of item hose 138. When blower motor starts on the HVAC system and low-pressure area 174 is created at the center of the venturi holes 14, antimicrobial fluid 124 may be drawn from reservoir 136 into the port area and injected into the air stream at this location. The plates for this kit are also coated with antimicrobial coating 18, like electrostatic antimicrobial coating 20. With the addition of the antibacterial liquid 124 to the air stream, and even more effective air purification may take place. The chemical agent, or antimicrobial liquid 124, can be changed out for different inhalation safe chemicals that can help to target specific bacteria and viruses. This air purification can lead to better overall air quality in the entire home or commercial space that is serviced by the HVAC unit 12. In addition, this method of purification does not require any modification to the existing HVAC system or components of that system.

In the specification and/or figures, typical embodiments of the disclosure have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein but is limited only by the following claims.

The invention claimed is:

1. An air decontamination apparatus for a common HVAC system comprising:
   a venturi plate device including a plurality of venturi holes therethrough, the venturi plate device with the plurality of venturi holes therethrough is configured to be positioned in the common HVAC system for forcing airflow in the common HVAC system through the plurality of venturi holes;
   each of the plurality of venturi holes including an antimicrobial coating, wherein the antimicrobial coating is an electrostatic antimicrobial coating applied to all surfaces of the air decontamination apparatus;
   each of the plurality of venturi holes including:
      a wide inlet portion;
      a narrow middle portion;
      a wide exhaust portion; and
      where the wide inlet portion tapers into the narrow middle portion and the narrow middle portion tapers out to the wide exhaust portion; and
   wherein, the venturi plate device is configured to be sealed between an inlet of the common HVAC system or an outlet of the common HVAC system for forcing the airflow of the common HVAC system through each of the plurality of venturi holes in the venturi plate device; and
   wherein, the air decontamination apparatus is configured to kill bacteria and viruses in the airflow in the common HVAC system via the antimicrobial coating on each of the plurality of venturi holes.

2. The air decontamination apparatus of claim 1, wherein the venturi plate device is sized and configured to be sealed to a duct of the common HVAC system in the inlet or the outlet of the common HVAC system via a foam seal around the venturi plate device.

3. The air decontamination apparatus of claim 1 further comprising:
   a mounting bracket, the mounting bracket is configured to secure the venturi plate device to be sealed between the inlet of the common HVAC system or the outlet of the common HVAC system.

4. The air decontamination apparatus of claim 3, wherein the mounting bracket is configured to be mounted inside a duct of the common HVAC system for sealing the venturi plate device to the duct.

5. The air decontamination apparatus of claim 4, wherein the mounting bracket including:
   an upper mount with an upper foam pad, the upper foam pad including an adhesive configured to secure the upper mount to a first portion of an inside of the duct;
   a lower mount with a lower foam pad, the lower foam pad including the adhesive configured to secure the lower mount to a second portion of the inside of the duct, where the second portion is on an opposite side of the duct from the first portion;
   an adjustable rod bracket connected between the upper mount and the lower mount; and
   a mounting plate connected to the adjustable rod bracket, the mounting plate is configured to secure the venturi plate device to the adjustable rod bracket connected between the upper mount and the lower mount.

6. The air decontamination apparatus of claim 5, wherein the adjustable rod bracket including:
   a pair of inner rods connected to the upper mount;
   a pair of outer rods connected to the lower mount; and
   the mounting plate including:
      an upper clamp plate including four upper half-round cuts and a plurality of threaded holes;
      a lower clamp plate including four lower half-round cuts configured to mirror the four upper half-round cuts, and a plurality of counterbore holes configured to align with the plurality of threaded holes in the upper clamp plate;
      a mounting alignment dowel protruding from the lower clamp plate;
      a mounting stud secured to the lower clamp plate through a center hole in the lower clamp plate;
      wherein, the mounting plate is configured to be adjustably secured to the pair of inner rods and the pair of outer rods via the lower clamp plate being secured to the upper clamp plate and squeezed around the pair of inner rods and the pair of outer rods in between the four upper half-round cuts and the four lower half-round cuts via a plurality of screws connected between the plurality of threaded holes in the upper clamp plate and the plurality of counterbore holes in the lower clamp plate;
      wherein, the mounting stud is configured to connect the venturi plate device to the mounting plate via a threaded connection to a knob with a knurled outer diameter; and
      wherein, the mounting alignment dowel is configured to align the venturi plate device about the mounting plate via an alignment hole in the venturi plate device.

7. The air decontamination apparatus of claim 1, wherein the venturi plate device including:
   an inlet venturi plate with the wide inlet portion of each of the plurality of venturi holes and a narrow inlet portion of the narrow middle portion of each of the plurality of venturi holes;
   an exhaust venturi plate with the wide exhaust portion of each of the plurality of venturi holes and a narrow exhaust portion of the narrow middle portion of each of the plurality of venturi holes;
   the narrow inlet portions of each of the narrow middle portions in the inlet venturi plate are aligned and fluidly connected to the narrow exhaust portions of each of the narrow middle portions of the exhaust venturi plate;
   a plate alignment dowel protruding from the inlet venturi plate and into an alignment hole of the exhaust venturi plate, or vice versa, the plate alignment dowel is configured to align each of the plurality of narrow inlet portions in the inlet venturi plate with each of the narrow exhaust portions in the exhaust venturi plate for creating the plurality of venturi holes therebetween; and
   wherein, the inlet venturi plate and the exhaust venturi plate are completely coated with the antimicrobial coating.

8. The air decontamination apparatus of claim 7, wherein the venturi plate device further comprising:

an intermediate antimicrobial plate positioned between the inlet venturi plate and the exhaust venturi plate, the intermediate antimicrobial plate including:
   a plurality of bladed holes configured to be positioned between the narrow inlet portions in the inlet venturi plate and the narrow exhaust portions in the exhaust venturi plate;
   each of the plurality of bladed holes including a plurality of turbulence blades, each of the plurality of turbulence blades including a sharp inlet edge angled toward a wider exit edge; and
   each of the plurality of turbulence blades of each of the plurality of bladed holes including the antimicrobial coating; and
   wherein, the intermediate antimicrobial plate is configured to swirl the airflow through the plurality of venturi holes.

9. The air decontamination apparatus of claim 8, wherein the intermediate antimicrobial plate further including:
   a center through hole configured to receive a mounting stud;
   an intermediate alignment hole configured to receive the plate alignment dowel therethrough, thereby aligning the plurality of bladed holes between the narrow inlet portions in the inlet venturi plate and the narrow exhaust portions in the exhaust venturi plate;
   the entire intermediate antimicrobial plate including the antimicrobial coating; and
   wherein, each of the plurality of bladed holes including eight turbulence blades equally spaced for creating a fan design.

10. The air decontamination apparatus of claim 7, wherein the venturi plate device further comprising an antimicrobial liquid injection system, the antimicrobial liquid injection system is configured to insert an antimicrobial liquid into the airflow moving through each of the venturi holes of the venturi plate device.

11. The air decontamination apparatus of claim 10, wherein the antimicrobial liquid injection system including:
   a liquid intermediate plate positioned between the inlet venturi plate and the exhaust venturi plate, the intermediate antimicrobial plate including:
      a plurality of injection holes configured to be positioned between the narrow inlet portions in the inlet venturi plate and the narrow exhaust portions in the exhaust venturi plate;
      each of the plurality of injection holes including at least one fluid port; and
   wherein, the liquid intermediate plate is configured to insert the antimicrobial liquid into the airflow through the plurality of venturi holes via the at least one fluid port in each of the plurality of injection holes.

12. The air decontamination apparatus of claim 11, wherein the liquid intermediate plate further including:
   at least one hose port configured to communicate with a hollow interior of the liquid intermediate plate;
   the hollow interior of the liquid intermediate plate fluidly connecting each of the at least one hose ports with each of the fluid ports in each of the plurality of injection holes;
   a center through hole configured to receive a mounting stud;
   an intermediate alignment hole configured to receive the plate alignment dowel therethrough, thereby aligning the plurality of injection holes between the narrow inlet portions in the inlet venturi plate and the narrow exhaust portions in the exhaust venturi plate;
   the entire liquid intermediate plate including the antimicrobial coating; and
   wherein, each of the plurality of injection holes including four fluid ports equally spaced around the injection hole, and each of the plurality of injection holes being angled from the wide inlet portions toward the wide exhaust portions of the venturi holes.

13. The air decontamination apparatus of claim 11, wherein the antimicrobial liquid injection system further comprising:
   a reservoir configured to hold the antimicrobial liquid;
   a hose connected between the reservoir and the at least one hose port of the liquid intermediate plate; and
   a reservoir mounting bracket configured to hold the reservoir and be mounted to the inside of a filter housing of the common HVAC system via adhesive strips.

14. The air decontamination apparatus of claim 13, wherein the antimicrobial liquid injection system further comprising:
   a fluid level sensor in the reservoir configured to sense an amount of the antimicrobial liquid inside of the reservoir; and
   a buzzer in communication with the fluid level sensor, the buzzer is configured to emit an alarm sound when the fluid level sensor senses the amount of the antimicrobial liquid inside of the reservoir is below a set refill amount.

15. The air decontamination apparatus of claim 14, wherein the antimicrobial liquid injection system further comprising:
   a battery configured to power the buzzer, the battery is mounted on the reservoir via a battery holder;
   a positive connector wire connected between a positive side of the battery and the buzzer;
   a first negative connector wire connected between a negative side of the battery and the fluid level sensor;
   a second negative connector wire connected between the fluid level sensor and the buzzer;
   the fluid level sensor is a normally closed fluid activated sensor configured to close when dry and open when wet; and
   a low fluid level warning kit cover attached to a bottom of the reservoir configured to house and seal the battery, buzzer, and the fluid level sensor.

16. The air decontamination apparatus of claim 11, wherein the antimicrobial liquid injection system is configured to allow the antimicrobial liquid to be drawn out of each of the fluid ports in each of the injection holes via low pressure created by the airflow of the common HVAC system.

17. An air decontamination apparatus for a common HVAC system comprising:
   a venturi plate device with a plurality of venturi holes configured to be positioned in the common HVAC system for forcing airflow in the common HVAC system through the plurality of venturi holes;
   each of the plurality of venturi holes including:
      a wide inlet portion;
      a narrow middle portion;
      a wide exhaust portion; and
      where the wide inlet portion tapers into the narrow middle portion and the narrow middle portion tapers out to the wide exhaust portion;
   an antimicrobial coating applied to all surfaces of the venturi plate device, the antimicrobial coating is an electrostatic antimicrobial coating;

the venturi plate device is configured to be sealed between an inlet of the common HVAC system or an outlet of the common HVAC system for forcing the airflow of the common HVAC system through each of the plurality of venturi holes in the venturi plate device, wherein the venturi plate device is sized and configured to be sealed to a duct of the common HVAC system in the inlet or the outlet of the common HVAC system via a foam seal around the venturi plate device;

the venturi plate device including:
  an inlet venturi plate with the wide inlet portion of each of the plurality of venturi holes and a narrow inlet portion of the narrow middle portion of each of the plurality of venturi holes;
  an exhaust venturi plate with the wide exhaust portion of each of the plurality of venturi holes and a narrow exhaust portion of the narrow middle portion of each of the plurality of venturi holes;
  the narrow inlet portions of each of the narrow middle portions in the inlet venturi plate are fluidly connected to the narrow exhaust portions of each of the narrow middle portions of the exhaust venturi plate; and
  a plate alignment dowel protruding from the inlet venturi plate and into an alignment hole of the exhaust venturi plate, or vice versa, the plate alignment dowel is configured to align each of the plurality of narrow inlet portions in the inlet venturi plate with each of the narrow exhaust portions in the exhaust venturi plate for creating the plurality of venturi holes therebetween; and
  an intermediate antimicrobial plate positioned between the inlet venturi plate and the exhaust venturi plate, the intermediate antimicrobial plate including:
    a plurality of bladed holes configured to be positioned between the narrow inlet portions in the inlet venturi plate and the narrow exhaust portions in the exhaust venturi plate;
    each of the plurality of bladed holes including a plurality of turbulence blades, each of the plurality of turbulence blades including a sharp inlet edge angled toward a wider exit edge; and
    each of the plurality of turbulence blades of each of the plurality of bladed holes including the antimicrobial coating;
    a center through hole configured to receive a mounting stud;
    an intermediate alignment hole configured to receive the plate alignment dowel therethrough, thereby aligning the plurality of bladed holes between the narrow inlet portions in the inlet venturi plate and the narrow exhaust portions in the exhaust venturi plate;
    wherein, each of the plurality of bladed holes including eight turbulence blades equally spaced for creating a fan design; and
    wherein, the intermediate antimicrobial plate is configured to swirl the airflow through the plurality of venturi holes; and
  wherein, the air decontamination apparatus is configured to kill bacteria and viruses in the airflow in the common HVAC system via the antimicrobial coating on each of the plurality of venturi holes.

18. An air decontamination apparatus for a common HVAC system comprising:

a venturi plate device with a plurality of venturi holes configured to be positioned in the common HVAC system for forcing airflow in the common HVAC system through the plurality of venturi holes;

each of the plurality of venturi holes including:

a wide inlet portion;

a narrow middle portion;

a wide exhaust portion; and where the wide inlet portion tapers into the narrow middle portion and the narrow middle portion tapers out to the wide exhaust portion;

an antimicrobial coating applied to all surfaces of the venturi plate device, the antimicrobial coating is an electrostatic antimicrobial coating;

the venturi plate device is configured to be sealed between an inlet of the common HVAC system or an outlet of the common HVAC system for forcing the airflow of the common HVAC system through each of the plurality of venturi holes in the venturi plate device, wherein the venturi plate device is sized and configured to be sealed to a duct of the common HVAC system in the inlet or the outlet of the common HVAC system via a foam seal around the venturi plate device;

the venturi plate device including:

an inlet venturi plate with the wide inlet portion of each of the plurality of venturi holes and a narrow inlet portion of the narrow middle portion of each of the plurality of venturi holes;

an exhaust venturi plate with the wide exhaust portion of each of the plurality of venturi holes and a narrow exhaust portion of the narrow middle portion of each of the plurality of venturi holes;

the narrow inlet portions of each of the narrow middle portions in the inlet venturi plate are fluidly connected to the narrow exhaust portions of each of the narrow middle portions of the exhaust venturi plate;

a plate alignment dowel protruding from the inlet venturi plate and into an alignment hole of the exhaust venturi plate, or vice versa, the plate alignment dowel is configured to align each of the plurality of narrow inlet portions in the inlet venturi plate with each of the narrow exhaust portions in the exhaust venturi plate for creating the plurality of venturi holes therebetween; and an antimicrobial liquid injection system, the antimicrobial liquid injection system is configured to insert an antimicrobial liquid into the airflow moving through each of the venturi holes of the venturi plate device, the antimicrobial liquid injection system including:

a liquid intermediate plate positioned between the inlet venturi plate and the exhaust venturi plate, the intermediate antimicrobial plate including:

a plurality of injection holes configured to be positioned between the narrow inlet portions in the inlet venturi plate and the narrow exhaust portions in the exhaust venturi plate;

each of the plurality of injection holes including at least one fluid port;

at least one hose port configured to communicate with a hollow interior of the liquid intermediate plate;

the hollow interior of the liquid intermediate plate fluidly connecting each of the at least one hose ports with each of the fluid ports in each of the plurality of injection holes;

an intermediate alignment hole configured to receive the plate alignment dowel therethrough, thereby aligning the plurality of injection holes between the narrow inlet portions in the inlet venturi plate and the narrow exhaust portions in the exhaust venturi plate;

the entire liquid intermediate plate including the antimicrobial coating; and wherein, each of the plurality of injection holes including four fluid ports equally spaced around the injection hole, and each of the plurality of injection holes being angled from the wide inlet portions toward the wide exhaust portions of the venturi holes;

wherein, the liquid intermediate plate is configured to insert the antimicrobial liquid into the airflow through the plurality of venturi holes via the at least one fluid port in each of the plurality of injection holes, wherein the antimicrobial liquid injection system is configured to allow the antimicrobial liquid to be drawn out of each of the fluid ports in each of the injection holes via low pressure created by the airflow of the common HVAC system; and wherein, the air decontamination apparatus is configured to kill bacteria and viruses in the airflow in the common HVAC system via the antimicrobial coating on each of the plurality of venturi holes and via the antimicrobial liquid from the antimicrobial liquid injection system.

* * * * *